(12) United States Patent
Aicher et al.

(10) Patent No.: US 8,633,201 B2
(45) Date of Patent: Jan. 21, 2014

(54) THIENOPYRIMIDINES HAVING MNK1/MNK2 INHIBITING ACTIVITY FOR PHARMACEUTICAL COMPOSITIONS

(75) Inventors: Babette Aicher, Frankfurt am Main (DE); Thomas Stephen Coulter, Wantage (GB); Stefan Jaekel, Darmstadt (DE); Arndt-René Kelter, Alfter (DE); Stephen Murfin, Didcot (GB); Tanja Reuter, Darmstadt (DE); Steven Taylor, Didcot (GB)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 685 days.

(21) Appl. No.: 12/296,427

(22) PCT Filed: Apr. 10, 2007

(86) PCT No.: PCT/EP2007/003186
§ 371 (c)(1),
(2), (4) Date: Oct. 13, 2009

(87) PCT Pub. No.: WO2007/115822
PCT Pub. Date: Oct. 18, 2007

(65) Prior Publication Data
US 2010/0056548 A1  Mar. 4, 2010

(30) Foreign Application Priority Data
Apr. 7, 2006 (EP) .................................. 06007454

(51) Int. Cl.
C07D 495/04 (2006.01)
A61K 31/519 (2006.01)
A61P 19/02 (2006.01)
A61P 17/06 (2006.01)
A61P 11/06 (2006.01)
A61P 29/00 (2006.01)

(52) U.S. Cl.
USPC ........................................ 514/260.1; 544/278

(58) Field of Classification Search
USPC ........................................ 544/278; 514/260.1
See application file for complete search history.

(56) References Cited

U.S. PATENT DOCUMENTS

| | | | |
|---|---|---|---|
| 5,686,457 A | 11/1997 | Traxler et al. | |
| 6,096,749 A | 8/2000 | Traxler et al. | |
| 6,265,410 B1 * | 7/2001 | Bridges et al. | 514/260.1 |
| 6,395,733 B1 | 5/2002 | Arnold et al. | |
| 6,784,174 B1 | 8/2004 | Cumming | |
| 2001/0027197 A1 | 10/2001 | Bridges | |
| 2003/0162795 A1 | 8/2003 | Munchhof | |
| 2006/0020042 A1 | 1/2006 | McDonald et al. | |
| 2007/0099877 A1 * | 5/2007 | Cai et al. | 514/151 |
| 2010/0015708 A1 | 1/2010 | Quay et al. | |
| 2010/0056548 A1 | 3/2010 | Aicher et al. | |
| 2010/0143341 A1 | 6/2010 | Taylor et al. | |
| 2010/0247517 A1 | 9/2010 | Austen et al. | |
| 2011/0021203 A1 | 1/2011 | Yamada et al. | |
| 2011/0212102 A1 | 9/2011 | Lehmann-Lintz et al. | |
| 2011/0217311 A1 | 9/2011 | Lehmann-Lintz et al. | |
| 2012/0128686 A1 | 5/2012 | Austen et al. | |
| 2013/0056914 A1 | 3/2013 | Frankowski et al. | |

FOREIGN PATENT DOCUMENTS

| | | |
|---|---|---|
| CA | 2038521 A1 | 9/1991 |
| CH | 408945 A | 3/1966 |
| DE | 248593 A1 | 8/1987 |
| EP | 0447891 A1 | 9/1991 |
| EP | 0452002 A2 | 10/1991 |
| EP | 0682027 A1 | 11/1995 |
| EP | 0729758 A2 | 9/1996 |
| EP | 1724268 A1 | 11/2006 |
| JP | 2005503345 A | 2/2005 |
| WO | 9413677 A1 | 6/1994 |
| WO | 9713771 A1 | 4/1997 |
| WO | 9924440 A1 | 5/1999 |
| WO | 0056738 A1 | 9/2000 |
| WO | 00/75145 A1 | 12/2000 |
| WO | 02088138 A1 | 11/2002 |
| WO | 03/037362 A2 | 5/2003 |
| WO | 2004037159 A2 | 5/2004 |
| WO | 2004/113347 A1 | 12/2004 |
| WO | 2004106340 A2 | 12/2004 |
| WO | 2005010008 A1 | 2/2005 |
| WO | 2005042537 A1 | 5/2005 |
| WO | 2005080377 A1 | 9/2005 |
| WO | 2005117890 A2 | 12/2005 |
| WO | 2006014325 A2 | 2/2006 |
| WO | 2006066937 A2 | 6/2006 |
| WO | 2006094791 A1 | 9/2006 |
| WO | 2006124874 A2 | 11/2006 |

(Continued)

OTHER PUBLICATIONS

Banker, G.S. et al, "Modern Pharmaceutics, 3ed.", Marcel Dekker, New York, 1996, p. 596.*
Wolff, Manfred E. "Burger's Medicinal Chemistry, 5ed, Part I", John Wiley & Sons, 1995, pp. 975-977.*
Munchhof, M.J., "Design and SAR of Thienopyrimidine and Thienopyridine Inhibitors of VEGFR-2 Kinase Activity," Bioorganic & Medicinal Chemistry Letters 14(1):21-24, Jan. 2004.
Showalter, H.D.H., "Tyrosine Kinase Inhibitors. 16. 6,5,6-Tricyclic Benzothieno[3,2-d]pyrimidines and Pyrimodo[5,4-b]- and -[4,5-b]indoles as Potent Inhibitors of the Epidermal Growth Factor Receptor Tyrosine Kinase," Journal of Medicinal Chemistry 42(26):5464-5474, Dec. 1999.

(Continued)

Primary Examiner — Susanna Moore
(74) Attorney, Agent, or Firm — Michael P. Morris; Edward S. Lazer

(57) ABSTRACT

The present invention relates to novel pharmaceutical compositions comprising thienopyrimidine compounds. Moreover, the present invention relates to the use of the thienopyrimidine compounds of the invention for the production of pharmaceutical compositions for the prophylaxis and/or treatment of diseases which can be influenced by the inhibition of the kinase activity of Mnk1 and/or Mnk2 (Mnk2a or Mnk2b) and/or variants thereof.

12 Claims, 5 Drawing Sheets

(56) References Cited

FOREIGN PATENT DOCUMENTS

| | | |
|---|---|---|
| WO | 2006136402 A1 | 12/2006 |
| WO | 2007056214 A2 | 5/2007 |
| WO | 2007056215 A2 | 5/2007 |
| WO | 2007059905 A2 | 5/2007 |
| WO | 2007081517 A2 | 7/2007 |
| WO | 2007084815 A2 | 7/2007 |
| WO | 2007115822 A1 | 10/2007 |
| WO | 2007147874 A1 | 12/2007 |
| WO | 2008006547 A2 | 1/2008 |
| WO | 2008041053 A2 | 4/2008 |
| WO | 2009065596 A2 | 5/2009 |
| WO | 2010023181 A1 | 3/2010 |
| WO | 2011104334 A1 | 9/2011 |
| WO | 2011104337 A1 | 9/2011 |
| WO | 2011104338 A1 | 9/2011 |
| WO | 2011104340 A1 | 9/2011 |

OTHER PUBLICATIONS

Sobolov, S.B., "Selective N-Alkylation of Pyrrolopyrimidines and Indoles by 'Transfer of Activation,'" Tetrahedron Letters 39(32):5685-5688, Aug. 1998.

Baumgartner, A., et al; Uber Thieno-Verbindungen: 14. Mitteilung: Darstellung 4-Aminosubstituierter Thieno[2.3-d]pyrimidyn-6-carbosa bsauurederivate; Institut fur Pharnazeutischer, 1993.

Cheng, C.C., et al; Potential Purine Antagonists. VI. Synthesis of 1-Alkyl- and 1-Aryl-4-substituted Pyrazolo[3,4-d] pyrimidines1,2; Journal of Organic Chemistry, American Chemical Society (1956) vol. 21 pp. 1240-1256.

Dörwald, Florencio Zaragoza, et al; Side Reactions in Organic Synthesis: A Guide to Successful Synthesys Design; (2005) Wiley; VCH, Weinheim p. IX of preface.

http://www.medterms.com/script/main/art.asp?articlekey=12063, last accessed on Aug. 24, 2010.

International Search Report for PCT/EP2006/005980 mailed Nov. 16, 2006.

International Search Report for PCT/EP2007/003186 mailed Jun. 8, 2007.

International Search Report for PCT/EP2007/006109 mailed Dec. 20, 2007.

International Search Report for PCT/EP2009/060876 mailed Nov. 10, 2009.

International Search Report for PCT/EP2011/052810 mailed May 16, 2011.

International Search Report for PCT/EP2011/052811/mailed May 18, 2011.

International Search Report for PCT/EP2011/052813 mailed May 30, 2011.

International Search Reportfor PCT/EP2008/009880 mailed Jun. 25, 2009.

Jorgensen, Anker, et al; Phosphorus Pentoxide in Organic Synthesis. XX [1]. Synthesis of N-Aryl-7H-pyrrolo [2,3-d]pyrimidin-4-amines; Journal of Heterocyclic Chemistry (1985) pp. 859-863.

Mogensen, Jorgen, et al; Phosphorus Pentoxide in Organic Synthesis: XXXIV*. Synthesis of 3-Arylthieno[2,3-d] pyrimidin-4(3H)-imines and their Rearrangement to N-arylthieno[2,3-d]pyrimidin-4-amines; Chemica Scripta (1988) vol. 28 pp. 195-200.

Peat, Andrew, J., et al; Novel Pyrazolopyrimidine Derivates as GSK-3 Inhibitors; Bioorganic & Medicinal Chemistry Letters (2004) vol. 14 pp. 2121-2125.

Traxler, Peter, et al; Use of a Pharmacophore Model for the Design of EGF-R Tyrosine Kinase Inhibitors: 4-(Phenylamino)pyrazolo[3,4-d]pyrimidines; Journal of Medicinal Chemistry (1997) vol. 40, No. 22 pp. 3601-3616.

Traxler, Peter, M., et at; 4-(Phenylamino)pyrrolopyrimidines: Potent and Selective, ATP Site Directed Inhibitors of the EGF-Receptor Protein Tyrosine Kinase; Journal of Medicinal Chemistry (1996) vol. 39 pp. 2285-2292.

West, R. A., et al; 2-Alkyl(aryl)-and2,7-Dimethyl-4-substituted Aminopyrrolo [2,3-d]pyrimidines; Journal of Organic Chemistry (1961) vol. 26 pp. 3809-3812.

Young, Rodney, C., et al; Purine Derivates as Competitive Inhibitors of Human Erythrocyte Membrane Phosphatidylinositol 4-Kinase; Journal of Medicinal Chemistry (1990) vol. 33 pp. 2073-2080.

* cited by examiner

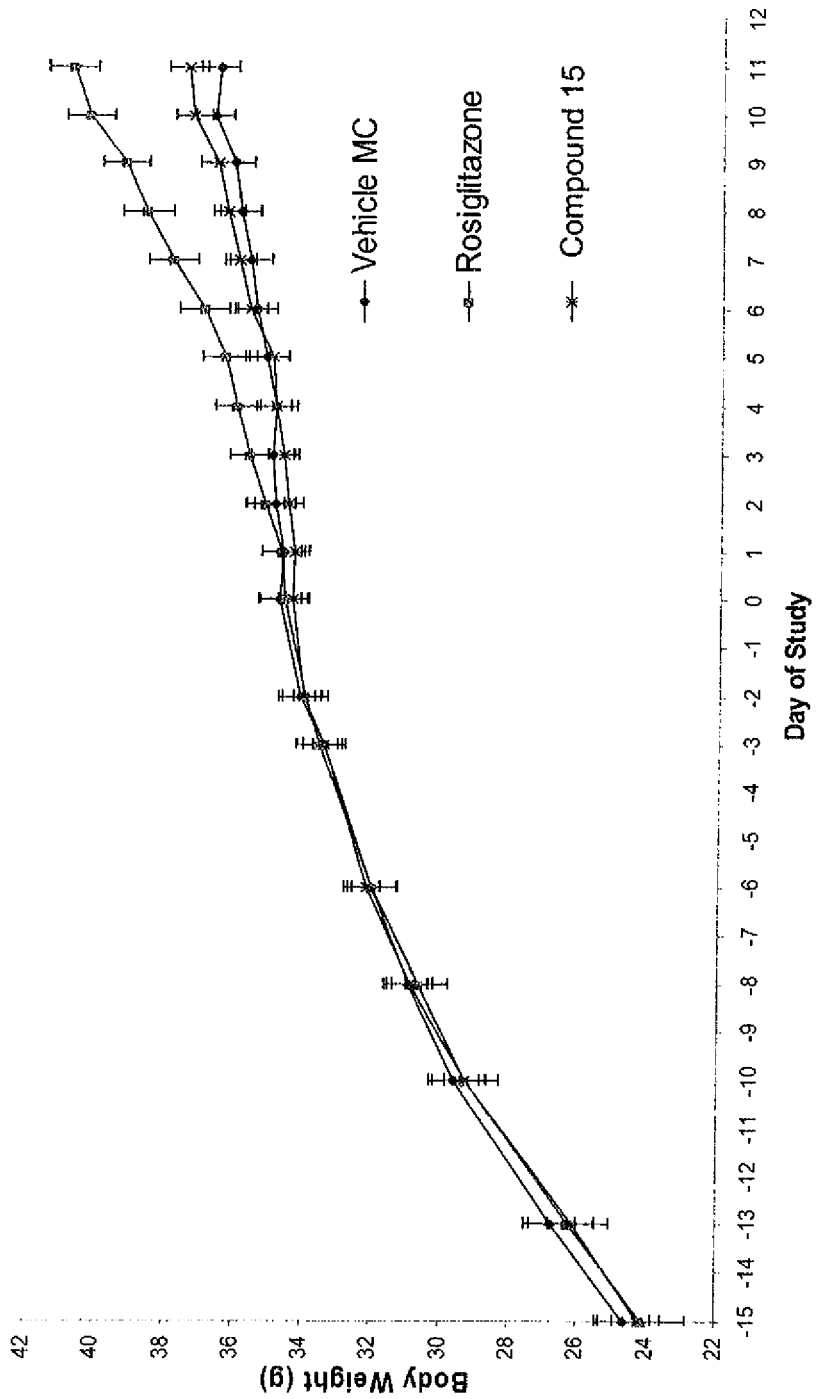
Fig. 1 Bodyweight Development

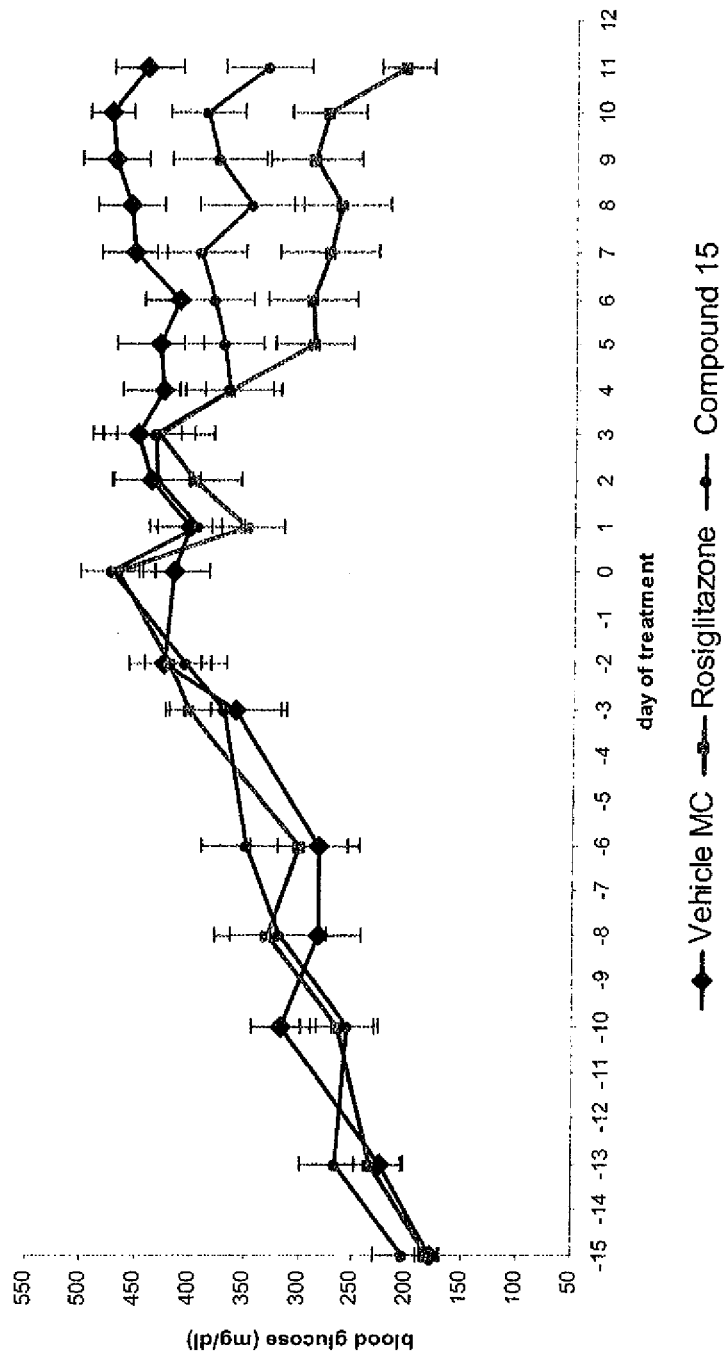

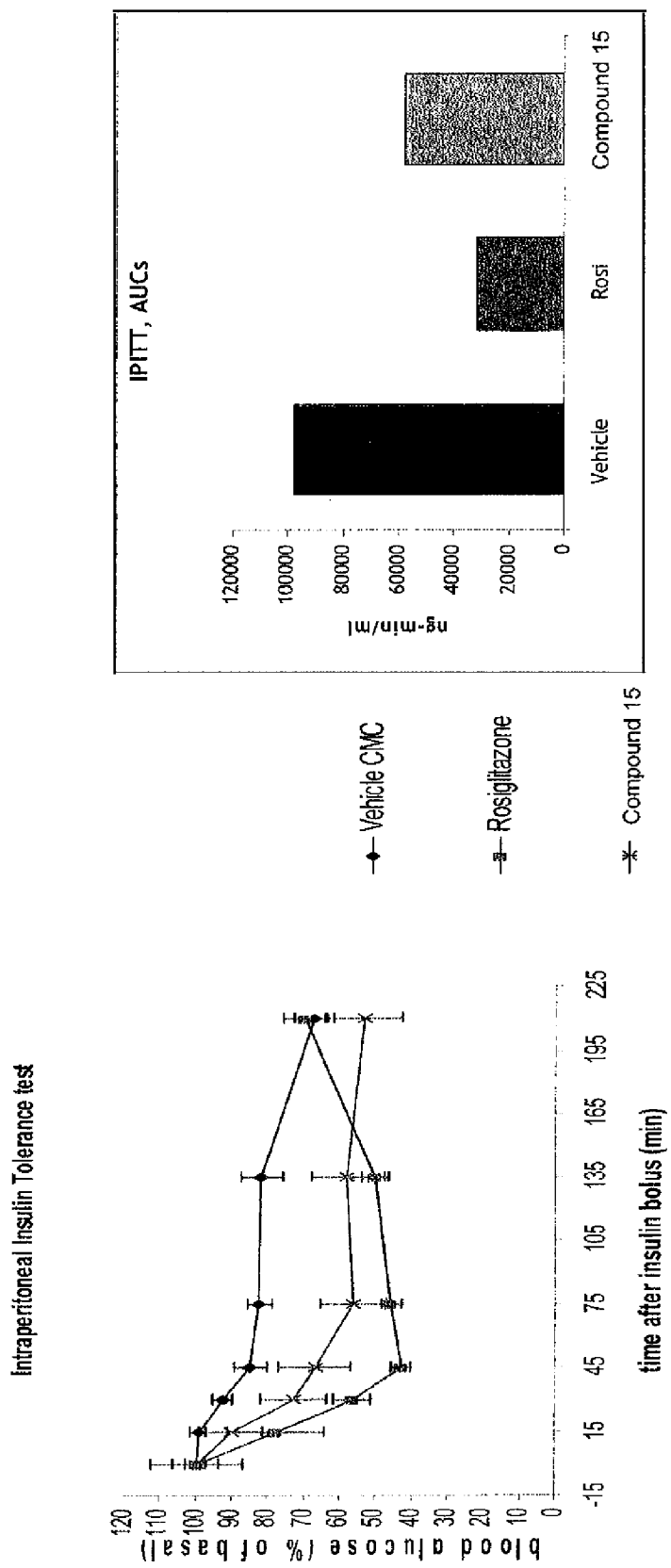
Fig. 3 Insulin Tolerance Test

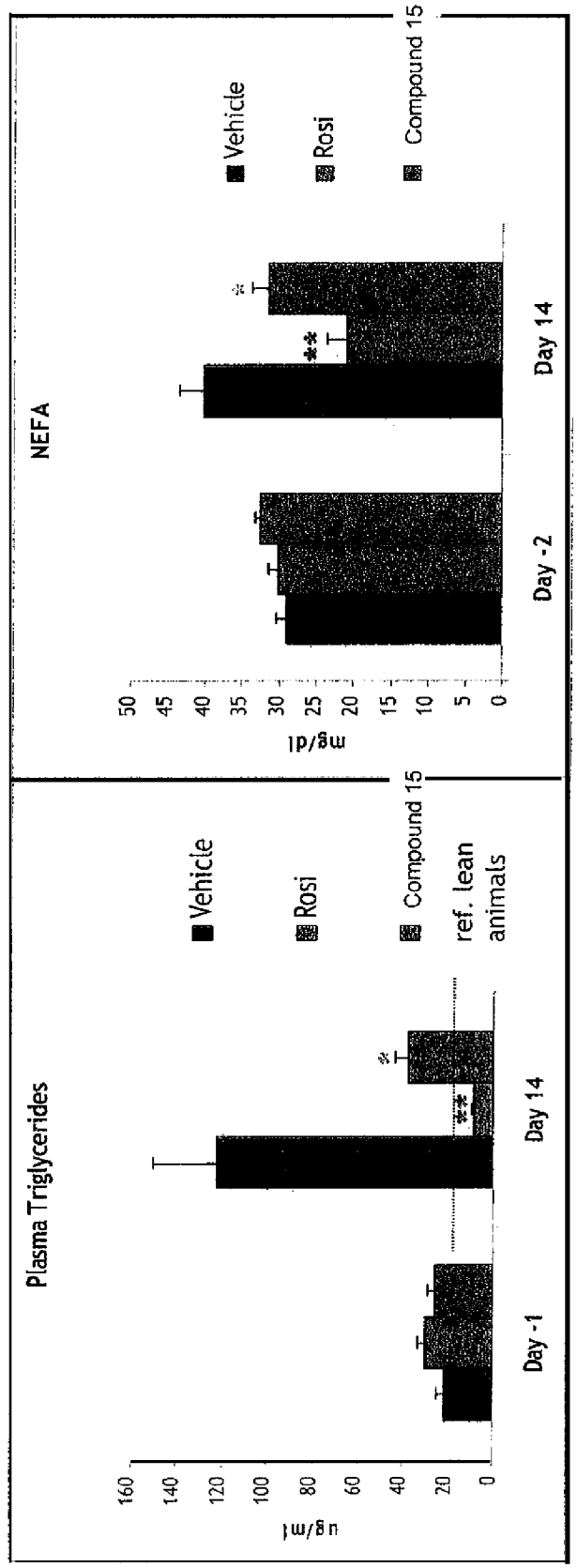
Fig. 4 Plasma triglycerides and free fatty acids

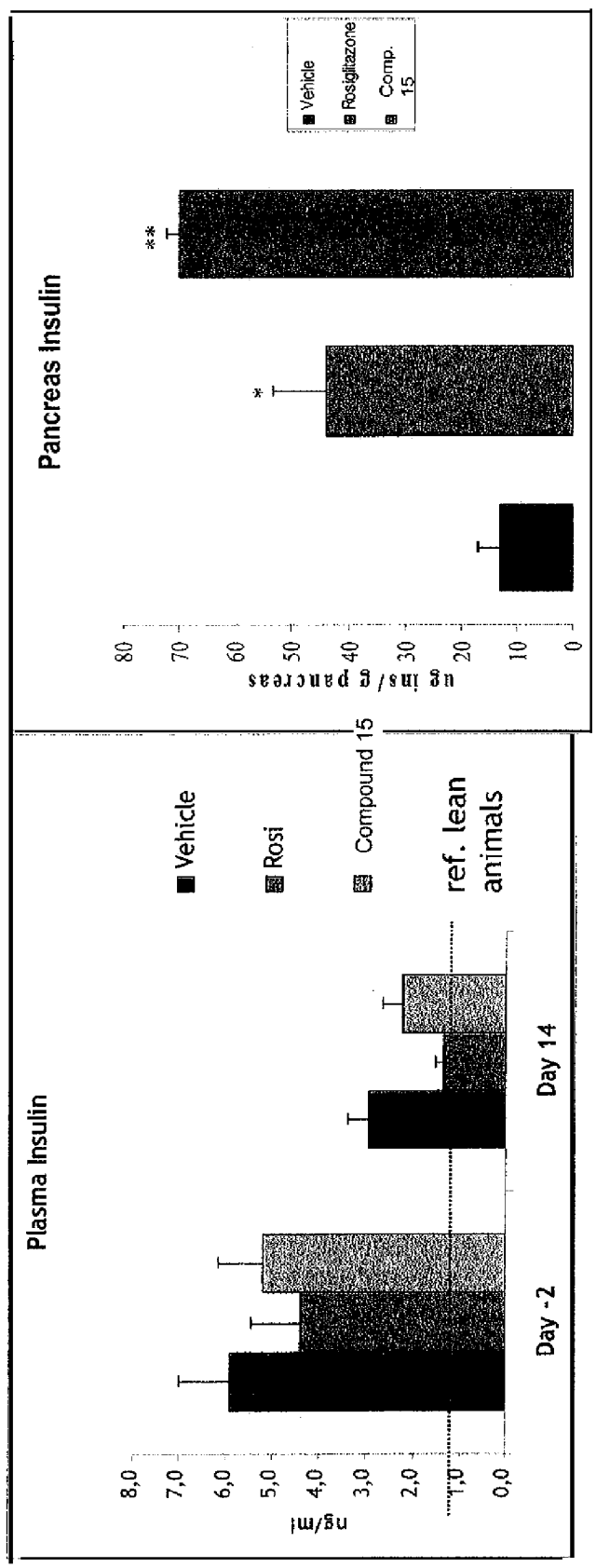
Fig. 5 Plasma insulin and pancreatic insulin

THIENOPYRIMIDINES HAVING MNK1/MNK2 INHIBITING ACTIVITY FOR PHARMACEUTICAL COMPOSITIONS

The present invention relates to thienopyrimidine compounds and to novel pharmaceutical compositions comprising thienopyrimidine compounds.

Moreover, the present invention relates to the use of the thienopyrimidine compounds of the invention for the production of pharmaceutical compositions for the prophylaxis and/or treatment of diseases which can be influenced by the inhibition of the kinase activity of Mnk1 (Mnk1a or MnK1b) and/or Mnk2 (Mnk2a or Mnk2b) or further variants thereof. Particularly, the present invention relates to the use of the thienopyrimidine compounds of the invention for the production of pharmaceutical compositions for the prophylaxis and/or therapy of metabolic diseases, such as diabetes, hyperlipidemia and obesity, hematopoietic disorders and cancer and their consecutive complications and disorders associated therewith.

Metabolic diseases are diseases caused by an abnormal metabolic process and may either be congenital due to an inherited enzyme abnormality or acquired due to a disease of an endocrine organ or failure of a metabolically important organ such as the liver or the pancreas.

The present invention is more particularly directed to the treatment and/or prophylaxis of in particular metabolic diseases of the lipid and carbohydrate metabolism and the consecutive complications and disorders associated therewith.

Lipid disorders cover a group of conditions which cause abnormalities in the level and metabolism of plasma lipids and lipoproteins. Thus, hyperlipidemias are of particular clinical relevance since they constitute an important risk factor for the development of atherosclerosis and subsequent vascular diseases such as coronary heart disease.

Diabetes mellitus is defined as a chronic hyperglycemia associated with resulting damages to organs and dysfunctions of metabolic processes. Depending on its etiology, one differentiates between several forms of diabetes, which are either due to an absolute (lacking or decreased insulin secretion) or to a relative lack of insulin. Diabetes mellitus Type I (IDDM, insulin-dependent diabetes mellitus) generally occurs in adolescents under 20 years of age. It is assumed to be of auto-immune etiology, leading to an insulitis with the subsequent destruction of the beta cells of the islets of Langerhans which are responsible for the insulin synthesis. In addition, in latent autoimmune diabetes in adults (LADA; Diabetes Care. 8: 1460-1467, 2001) beta cells are being destroyed due to autoimmune attack. The amount of insulin produced by the remaining pancreatic islet cells is too low, resulting in elevated blood glucose levels (hyperglycemia). Diabetes mellitus Type II generally occurs at an older age. It is above all associated with a resistance to insulin in the liver and the skeletal muscles, but also with a defect of the islets of Langerhans. High blood glucose levels (and also high blood lipid levels) in turn lead to an impairment of beta cell function and to an increase in beta cell apoptosis.

Diabetes is a very disabling disease, because today's common anti-diabetic drugs do not control blood sugar levels well enough to completely prevent the occurrence of high and low blood sugar levels. Out of range blood sugar levels are toxic and cause long-term complications for example retinopathy, renopathy, neuropathy and peripheral vascular disease. There is also a host of related conditions, such as obesity, hypertension, heart disease and hyperlipidemia, for which persons with diabetes are substantially at risk.

Obesity is associated with an increased risk of follow-up diseases such as cardiovascular diseases, hypertension, diabetes, hyperlipidemia and an increased mortality. Diabetes (insulin resistance) and obesity are part of the "metabolic syndrome" which is defined as the linkage between several diseases (also referred to as syndrome X, insulin-resistance syndrome, or deadly quartet). These often occur in the same patients and are major risk factors for development of diabetes type II and cardiovascular disease. It has been suggested that the control of lipid levels and glucose levels is required to treat diabetes type II, heart disease, and other occurrences of metabolic syndrome (see e.g., Diabetes 48: 1836-1841, 1999; JAMA 288: 2209-2716, 2002).

In one embodiment of the present invention the compounds and compositions of the present invention are useful for the treatment and/or prophylaxis of metabolic diseases of the carbohydrate metabolism and their consecutive complications and disorders such as impaired glucose tolerance, diabetes (preferably diabetes type II), diabetic complications such as diabetic gangrene, diabetic arthropathy, diabetic osteopenia, diabetic glomerosclerosis, diabetic nephropathy, diabetic dermopathy, diabetic neuropathy, diabetic cataract and diabetic retinopathy, diabetic maculopathy, diabetic feet syndrome, diabetic coma with or without ketoacidosis, diabetic hyperosmolar coma, hypoglycemic coma, hyperglycemic coma, diabetic acidosis, diabetic ketoacidosis, intracapillary glomerulonephrosis, Kimmelstiel-Wilson syndrome, diabetic amyotrophy, diabetic autonomic neuropathy, diabetic mononeuropathy, diabetic polyneuropathy, diabetic angiopathies, diabetic peripheral angiopathy, diabetic ulcer, diabetic arthropathy, or obesity in diabetes.

In a further embodiment the compounds and compositions of the present invention are useful for the treatment and/or prophylaxis of metabolic diseases of the lipid metabolism (i.e. lipid disorders) and their consecutive complications and disorders such as hypercholesterolemia, familial hypercholesterolemia, Fredrickson's hyperlipoproteinemia, hyperbetalipoproteinemia, hyperlipidemia, low-density-lipoprotein-type [LDL] hyperlipoproteinemia, pure hyperglyceridemia, endogenous hyperglyceridemia, isolated hypercholesterolemia, isolated hypertroglyceridemia, cardiovascular diseases such as hypertension, ischemia, varicose veins, retinal vein occlusion, atherosclerosis, angina pectoris, myocardial infarction, stenocardia, pulmonary hypertension, congestive heart failure, glomerulopaty, tubulointestitial disorders, renal failure, angiostenosis, or cerebrovascular disorders, such as cerebral apoplexy.

In a further embodiment of the present invention the compounds and compositions of the present invention are useful for the treatment and/or prophylaxis of hematopoetic disorders and their consecutive complications and disorders such as acute myeloid leukemia (AML), Morbus Hodgkin, Non-Hodgkin's lymphoma; hematopoetic disease, acute non-lymphocytic leukemia (ANLL), myeloproliferative disease acute promyelocytic leukemia (APL), acute myelomonocytic leukemia (AMMoL), polycythemia vera, lymphoma, acute lymphocytic leukemia (ALL), chronic lymphocytic leukemia (CCL), Wilm's tumor, or Ewing's Sarcoma.

In a further embodiment of the present invention the compounds and compositions of the present invention are useful for the treatment and/or prophylaxis of cancer and consecutive complications and disorders such as cancer of the upper gastrointestinal tract, pancreatic carcinoma, breast cancer, colon cancer, ovarian carcinoma, cervix carcinoma, corpus carcinoma, brain tumor, testicular cancer, laryngeal carcinoma, osteocarcinoma, prostatic cancer, retinoblastoma, liver carcinoma, lung cancer, neuroblastoma, renal carcinoma, thyroid carcinoma, espohageal cancer, soft tissue sarcoma, cachexia, or pain.

Furthermore, the present invention relates to the use of thienopyrimidine compounds for the production of pharmaceutical compositions for the prophylaxis and/or therapy of cytokine related diseases.

Such diseases are i.a. inflammatory diseases, autoimmune diseases, destructive bone disorders, proliferative disorders, infectious diseases, neurodegenerative diseases, allergies, or other conditions associated with proinflammatory cytokines.

Allergic and inflammatory diseases such as acute or chronic inflammation, chronic inflammatory arthritis, rheumatoid arthritis, psoriasis, COPD, inflammatory bowel disease, asthma and septic shock and their consecutive complications and disorders associated therewith.

Inflammatory diseases like rheumatoid arthritis, inflammatory lung diseases like COPD, inflammatory bowel disease and psoriasis afflict one in three people in the course of their lives. Not only do those diseases impose immense health care costs, but also they are often crippling and debilitating.

Although inflammation is the unifying pathogenic process of these inflammatory diseases below, the current treatment approach is complex and is generally specific for any one disease. Many of the current therapies available today only treat the symptoms of the disease and not the underlying cause of inflammation.

The compositions of the present invention are useful for the treatment and/or prophylaxis of inflammatory diseases and consecutive complications and disorders. such as chronic or acute inflammation, inflammation of the joints such as chronic inflammatory arthritis, rheumatoid arthritis, psoriatic arthritis, osteoarthritis, juvenile rheumatoid arthritis, Reiter's syndrome, rheumatoid traumatic arthritis, rubella arthritis, acute synovitis and gouty arthritis; inflammatory skin diseases such as sunburn, psoriasis, erythrodermic psoriasis, pustular psoriasis, eczema, dermatitis, acute or chronic graft formation, atopic dermatitis, contact dermatitis, urticaria and scleroderma; inflammation of the gastrointestinal tract such as inflammatory bowel disease, Crohn's disease and related conditions, ulcerative colitis, colitis, and diverticulitis; nephritis, urethritis, salpingitis, oophoritis, endomyometritis, spondylitis, systemic lupus erythematosus and related disorders, multiple sclerosis, asthma, meningitis, myelitis, encephalomyelitis, encephalitis, phlebitis, thrombophiebitis, respiratory diseases such as asthma, bronchitis, chronic obstructive pulmonary disease (COPD), inflammatory lung disease and adult respiratory distress syndrome, and allergic rhinitis; endocarditis, osteomyelitis, rheumatic fever, rheumatic pericarditis, rheumatic endocarditis, rheumatic myocarditis, rheumatic mitral valve disease, rheumatic, aortic valve disease, prostatitis, prostatocystitis, spondoarthropathies ankylosing spondylitis, synovitis, tenosynovotis, myositis, pharyngitis, polymyalgia rheumatica, shoulder tendonitis or bursitis, gout, pseudo gout, vasculitides, inflammatory diseases of the thyroid selected from granulomatous thyroiditis, lymphocytic thyroiditis, invasive fibrous thyroiditis, acute thyroiditis; Hashimoto's thyroiditis, Kawasaki's disease, Raynaud's phenomenon, Sjogren's syndrome, neuroinflammatory disease, sepsis, conjunctivitis, keratitis, iridocyclitis, optic neuritis, otitis, lymphoadenitis, nasopaharingitis, sinusitis, pharyngitis, tonsillitis, laryngitis, epiglottitis, bronchitis, pneumonitis, stomatitis, gingivitis, oesophagitis, gastritis, peritonitis, hepatitis, cholelithiasis, cholecystitis, glomerulonephritis, goodpasture's disease, crescentic glomerulonephritis, pancreatitis, endomyometritis, myometritis, metritis, cervicitis, endocervicitis, exocervicitis, parametritis, tuberculosis, vaginitis, vulvitis, silicosis, sarcoidosis, pneumoconiosis, pyresis, inflammatory polyarthropathies, psoriatric arthropathies, intestinal fibrosis, bronchiectasis and enteropathic arthropathies.

Moreover, cytokines are also believed to be implicated in the production and development of various cardiovascular and cerebrovascular disorders such as congestive heart disease, myocardial infarction, the formation of atherosclerotic plaques, hypertension, platelet aggregation, angina, stroke, Alzheimer's disease, reperfusion injury, vascular injury including restenosis and peripheral vascular disease, and, for example, various disorders of bone metabolism such as osteoporosis (including senile and postmenopausal osteoporosis), Paget's disease, bone metastases, hypercalcaemia, hyperparathyroidism, osteosclerosis, osteoporosis and periodontitis, and the abnormal changes in bone metabolism which may accompany rheumatoid arthritis and osteoarthritis.

Excessive cytokine production has also been implicated in mediating certain complications of bacterial, fungal and/or viral infections such as endotoxic shock, septic shock and toxic shock syndrome and in mediating certain complications of CNS surgery or injury such as neurotrauma and ischaemic stroke.

Excessive cytokine production has, moreover, been implicated in mediating or exacerbating the development of diseases involving cartilage or muscle resorption, pulmonary fibrosis, cirrhosis, renal fibrosis, the cachexia found in certain chronic diseases such as malignant disease and acquired immune deficiency syndrome (AIDS), tumour invasiveness and tumour metastasis and multiple sclerosis. The treatment and/or prophylaxis of these diseases are also contemplated by the present invention Additionally, the inventive compositions may be used to treat inflammation associated with autoimmune diseases including, but not limited to, systemic lupus erythematosis, Addison's disease, autoimmune polyglandular disease (also known as autoimmune polyglandular syndrome), glomerulonephritis, rheumatoid arthritis scleroderma, chronic thyroiditis, Graves' disease, autoimmune gastritis, diabetes, autoimmune hemolytic anemia, glomerulonephritis, rheumatoid arthritis autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, and graft vs. host disease.

In a further embodiment the compositions of the present invention may be used for the treatment and prevention of infectious diseases such as sepsis, septic shock, Shigellosis, and *Helicobacter pylori* and viral diseases including herpes simplex type 1 (HSV-1), herpes simplex type 2 (HSV-2), cytomegalovirus, Epstein-Barr, human immunodeficiency virus (HIV), acute hepatitis infection (including hepatitis A, hepatits B, and hepatitis C), HIV infection and CMV retinitis, AIDS or malignancy, malaria, mycobacterial infection and meningitis. These also include viral infections, by influenza virus, varicella-zoster virus (VZV), Epstein-Barr virus, human herpesvirus-6 (HHV-6), human herpesvirus-7 (HHV-7), human herpesvirus-8 (HHV-8), pseudorabies and rhinotracheitis.

The compositions of the present invention may also be used topically in the treatment or prophylaxis of topical disease states mediated by or exacerbated by excessive cytokine production, such as inflamed joints, eczema, psoriasis and other inflammatory skin conditions such as sunburn; inflammatory eye conditions including conjunctivitis; pyresis, pain and other conditions associated with inflammation.

Periodontal disease has also been implemented in cytokine production, both topically and systemically. Hence, use of compositions of the present invention to control the inflammation associated with cytokine production in such peroral diseases such as gingivitis and periodontitis is another aspect of the present invention.

Finally, the compositions of the present invention may also be used to treat or prevent neurodegenerative disease selected from Alzheimer's disease, Parkinson's disease, amyotrophic lateral sclerosis, Huntington's disease, cerebral ischemia or neurodegenerative disease caused by traumatic injury, glutamate neurotoxicity or hypoxia.

In a preferred embodiment the compositions of the present invention may be used to treat or prevent a disease selected from chronic or acute inflammation, chronic inflammatory arthritis, rheumatoid arthritis, psoriasis, COPD, inflammatory bowel disease, septic shock, Crohn's disease, ulcerative colitis, multiple sclerosis and asthma.

Protein kinases are important enzymes involved in the regulation of many cellular functions. The LK6-serine/threonine-kinase gene of Drosophila melanogaster was described as a short-lived kinase which can associate with microtubules (J. Cell Sci. 1997, 110(2): 209-219). Genetic analysis in the development of the compound eye of Drosophila suggested a role in the modulation of the RAS signal pathway (Genetics 2000 156(3): 1219-1230). The closest human homologues of Drosophila LK6-kinase are the MAP-kinase interacting kinase 2 (Mnk2, e.g. the variants Mnk2a and Mnk2b) and MAP-kinase interacting kinase 1 (Mnk1) and variants thereof. These kinases are mostly localized in the cytoplasm. Mnks are phosphorylated by the p42 MAP kinases Erk1 and Erk2 and the p38-MAP kinases. This phosphorylation is triggered in a response to growth factors, phorbol esters and oncogenes such as Ras and Mos, and by stress signaling molecules and cytokines. The phosphorylation of Mnk proteins stimulates their kinase activity towards eukaryotic initiation factor 4E (eIF4E) (EMBO J. 16: 1909-1920, 1997; Mol Cell Biol 19, 1871-1880, 1990; Mol Cell Biol 21, 743-754, 2001). Simultaneous disruption of both, the Mnk1 and Mnk2 gene in mice diminishes basal and stimulated eIF4E phosphorylation (Mol Cell Biol 24, 6539-6549, 2004). Phosphorylation of eIF4E results in a regulation of the protein translation (Mol Cell Biol 22: 5500-5511, 2001).

There are different hypotheses describing the mode of the stimulation of the protein translation by Mnk proteins. Most publications describe a positive stimulatory effect on the cap-dependent protein translation upon activation of MAP kinase-interacting kinases. Thus, the activation of Mnk proteins can lead to an indirect stimulation or regulation of the protein translation, e.g. by the effect on the cytosolic phospholipase 2 alpha (BBA 1488:124-138, 2000).

WO 03/037362 discloses a link between human Mnk genes, particularly the variants of the human Mnk2 genes, and diseases which are associated with the regulation of body weight or thermogenesis. It is postulated that human Mnk genes, particularly the Mnk2 variants are involved in diseases such as e.g. metabolic diseases including obesity, eating disorders, cachexia, diabetes mellitus, hypertension, coronary heart disease, hypercholesterolemia, dyslipidemia, osteoarthritis, biliary stones, cancer of the genitals and sleep apnea, and in diseases connected with the ROS defense, such as e.g. diabetes mellitus and cancer. WO 03/03762 moreover discloses the use of nucleic acid sequences of the MAP kinase-interacting kinase (Mnk) gene family and amino acid sequences encoding these and the use of these sequences or of effectors of Mnk nucleic acids or polypeptides, particularly Mnk inhibitors and activators in the diagnosis, prophylaxis or therapy of diseases associated with the regulation of body weight or thermogenesis.

WO 02/103361 describes the use of kinases 2a and 2b (Mnk2a and Mnk2b) interacting with the human MAP kinase in assays for the identification of pharmacologically active ingredients, particularly useful for the treatment of diabetes mellitus type 2. Moreover, WO 02/103361 discloses also the prophylaxis and/or therapy of diseases associated with insulin resistance, by modulation of the expression or the activity of Mnk2a or Mnk2b. Apart from peptides, peptidomimetics, amino acids, amino acid analogues, polynucleotides, polynucleotide analogues, nucleotides and nucleotide analogues, 4-hydroxybenzoic acid methyl ester are described as a substance which binds the human Mnk2 protein.

Inhibitors of Mnk (referred to as CGP57380 and CGP052088) have been described (cf. Mol. Cell. Biol. 21, 5500, 2001; Mol Cell Biol Res Comm 3, 205, 2000; Genomics 69, 63, 2000). CGP052088 is a staurosporine derivative having an $IC_{50}$ of 70 nM for inhibition of in vitro kinase activity of Mnk1. CGP57380 is a low molecular weight selective, non-cytotoxic inhibitor of Mnk2 (Mnk2a or Mnk2b) or of Mnk1: The addition of CGP57380 to cell culture cells, transfected with Mnk2 (Mnk2a or Mnk2b) or Mnk1 showed a strong reduction of phosphorylated eIF4E.

First evidence for a role of Mnks in inflammation was provided by studies demonstrating activation of Mnk1 by proinflammatory stimuli. The cytokines TNFα and IL-1β trigger the activation of Mnk1 in vitro (Fukunaga and Hunter, EMBO J. 16(8): 1921-1933, 1997) and induce the phosphorylation of the Mnk-specific substrate eIF4E in vivo (Ueda et al., Mol Cell Biol 24(15): 6539-6549, 2004). In addition, administration of lipopolysaccharide (LPS), a potent stimulant of the inflammatory response, induces activation of Mnk1 and Mnk2 in mice, concomitant with a phosphorylation of their substrate eIF4E (Ueda et al., Mol Cell Biol 24(15): 6539-6549, 2004).

Furthermore, Mnk1 has been shown to be involved in regulating the production of proinflammatory cytokines. Mnk1 enhances expression of the chemokine RANTES (Nikolcheva et al., J Clin Invest 110, 119-126, 2002). RANTES is a potent chemotractant of monocytes, eosinophils, basophiles and, natural killer cells. It activates and induces proliferation of T lymphocytes, mediates degranulation of basophils and induces the respiratory burst in eosinophils (Conti and DiGioacchino, Allergy Asthma Proc 22(3):133-7, 2001)

WO 2005/00385 and Buxade et al., Immunity 23: 177-189, August 2005 both disclose a link between Mnks and the control of TNFα biosynthesis. The proposed mechanism is mediated by a regulatory AU-rich element (ARE) in the TNFα mRNA. Buxade et al. demonstrate proteins binding and controlling ARE function to be phosphorylated by Mnk1 and Mnk2. Specifically Mnk-mediated phosphorylation of the ARE-binding protein hnRNP A1 has been suggested to enhance translation of the TNFα mRNA.

TNFα is not the only cytokine regulated by an ARE. Functional AREs are also found in the transcripts of several interleukins, interferones and chemokines (Khabar, J Interf Cytokine Res 25: 1-10, 2005). The Mnk-mediated phosphorylation of ARE-binding proteins has thus the potential to control biosynthesis of cytokines in addition to that of TNFα.

Current evidence demonstrates Mnks as down stream targets of inflammatory signalling as well as mediators of the inflammatory response. Their involvement in the production of TNFα, RANTES, and potentially additional cytokines suggests inhibition of Mnks as strategy for anti-inflammatory therapeutic intervention.

The problem underlying the present invention is to provide potent and selective Mnk1 and/or Mnk2 inhibitors which may effectively and safely be used for the treatment of metabolic diseases, inflammatory diseases and their consecutive complication and disorders.

It has now been surprisingly found that certain thienopyrimidine compounds are potent inhibitors of the kinase enzymes Mnk1 and/or Mnk2 and/or variants thereof and as such may be useful in the prophylaxis and/or therapy of diseases which can be influenced by the inhibition of the kinase activity of Mnk1 and/or Mnk2 (Mnk2a or Mnk2b) and/or variants thereof.

BRIEF DESCRIPTION OF THE DRAWINGS

FIG. 1 shows the bodyweight development of mice before and after treatment with Rosiglitazone or Compound 15 in comparison with animals receiving only the Vehicle methylcellulose (MC). FIG. 2 shows the blood glucose development of mice before and after treatment with Rosiglitazone or Compound 15 in comparison with animals receiving only the Vehicle methylcellulose (MC). FIG. 3 shows the results of the Insulin Tolerance Test for mice receiving either Rosiglitazone or Compound 15 as well as for animals receiving only the Vehicle methylcellulose (MC). FIG. 4 shows the concentration of plasma triglycerides and free fatty acids in mice treated with either Rosiglitazone or Compound 15 as well as in mice receiving only the vehicle methylcellulose (MC) at the beginning and at the end of the study. FIG. 5 shows the concentration of plasma insulin and pancreatic insulin in mice treated with either Rosiglitazone or Compound 15 as well as in mice receiving only the vehicle methylcellulose (MC) at the beginning (only plasma insulin) and at the end (both plasma and pancreatic insulin) of the study.

DETAILED DESCRIPTION OF THE INVENTION)

Thienopyrimidine compounds of the present invention are compounds of the general formula (1):

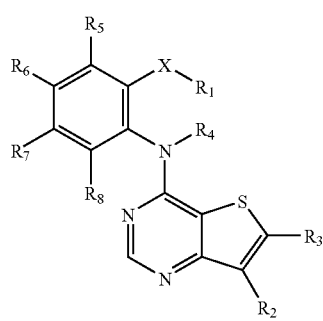

(1)

wherein X is a single bond, O, S, $SO_2$, $CH_2$, $CHR_{1a}$, $CR_{1a}R_{1b}$, CH(halogen), C(halogen)$_2$, C=O, C(O)$NR_{1a}$, NH or $NR_{1a}$, wherein $R_{1a}$ and $R_{1b}$ are $C_{1-6}$ alkyl, $C_{1-6}$ alkyl $C_{3-10}$ cycloalkyl, $C_{3-10}$ cycloalkyl, $C_{1-6}$ alkyl 3 to 10 membered heterocycloalkyl comprising at least one heteroatom selected from N, S and O, 3 to 10 membered heterocycloalkyl comprising at least one heteroatom selected from N, S and O, wherein $R_{1a}$ and $R_{1b}$ are optionally substituted with one or more $R_9$, $R_1$ is hydrogen, $C_{1-6}$ alkyl, $C_{1-6}$alkyl $C_{3-10}$ cycloalkyl, $C_{3-10}$ cycloalkyl, $C_{1-6}$ alkyl 3 to 10 membered heterocycloalkyl comprising at least one heteroatom selected from N, S and O, 3 to 10 membered heterocycloalkyl comprising at least one heteroatom selected from N, S and O, $C_{6-10}$ aryl, $C_{1-6}$ alkyl $C_{6-10}$ aryl, $C_{5-10}$ heteroaryl comprising at least one heteroatom selected from N, S and O, $C_{1-6}$ alkyl $C_{5-10}$ heteroaryl comprising at least one heteroatom selected from N, S and O; wherein $R_1$ is optionally substituted with one or more $R_9$;

or if X is $NR_{1a}$, $CHR_{1a}$, C(O)$NR_{1a}$ or $CR_{1a}R_{1b}$, $R_1$ may form a 5 or 6 membered saturated, unsaturated or aromatic carbocyclic or heterocyclic ring with $R_{1a}$ and the N or C atom to which they are attached, which rings may contain one or more additional heteroatoms selected from N, S and O, which may be substituted with one or more $R_9$;

$R_2$ and $R_3$ are the same or different and are independently selected from hydrogen, $C_{1-6}$ alkyl, $C_{1-6}$ alkyl $C_{3-10}$ cycloalkyl, $C_{3-10}$ cycloalkyl, $C_{6-10}$ aryl, $C_{1-6}$ alkyl $C_{6-10}$ aryl, $C_{5-10}$ heteroaryl comprising at least one heteroatom selected from N, S and O, $C_{1-6}$ alkyl $C_{5-10}$ heteroaryl comprising at least one heteroatom selected from N, S and O, $C_{1-6}$ alkyl 3 to 10 membered heterocycloalkyl comprising at least one heteroatom selected from N, S and O, 3 to 10 membered heterocycloalkyl comprising at least one heteroatom selected from N, S and O, or together with the C atoms that they are attached to form a $C_{3-7}$ cycloalkyl or a 3 to 10 membered heterocycloalkyl group, wherein $R_2$ and $R_3$ are optionally substituted with one or more $R_9$; $R_2$ may also be $R_9$ and $R_3$ may also be halogen; CN; $OR_{11}$; $S(O)_2N(R_{11}R_{11a})$; $S(O)N(R_{11}R_{11a})$; $S(O)_2R_{11}$; $N(R_{11})S(O)_2N(R_{11a}R_{11b})$; $SR_{11}$; $N(R_{11}R_{11a})$; $OC(O)R_{11}$; $N(R_{11})C(O)R_{11a}$; $N(R_{11})S(O)_2R_{11a}$; $N(R_{11})S(O)R_{11a}$; $N(R_{11})C(O)N(R_{11a}R_{11b})$; $N(R_{11})C(O)OR_{11a}$; $OC(O)N(R_{11}R_{11a})$; oxo (=O), where the ring is at least partially saturated; C(O)$R_{11}$; $C_{1-6}$ alkyl; phenyl; $C_{3-7}$ cycloalkyl; or heterocyclyl; wherein $C_{1-6}$ alkyl, phenyl, $C_{3-7}$ cycloalkyl, and heterocyclyl are optionally substituted with one or more $R_9$.

$R_4$ is hydrogen, $C_{1-4}$ alkyl, urea, thiourea or acetyl optionally substituted with one or more $R_9$;

or $R_4$ may form a 5 or 6 membered saturated, unsaturated or aromatic heterocyclic ring with X;

$R_5$, $R_6$, $R_7$ and $R_8$ are the same or different and are independently selected from hydrogen and $R_9$;

or $R_6$ and $R_7$ may form a 5 or 6 membered saturated, unsaturated or aromatic carbocyclic or heterocyclic ring wherein the heterocyclic ring comprises at least one heteroatom selected from N, S and O;

$R_9$ is independently halogen; CN; COOR$_{11}$; OR$_{11}$; C(O)N$(R_{11}R_{11a})$; S(O)$_2$N$(R_{11}R_{11a})$; S(O)N$(R_{11}R_{11a})$; S(O)$_2R_{11}$; N(R$_{11}$)S(O)$_2$N$(R_{11a}R_{11})$; SR$_{11}$; N(R$_{11}R_{11a}$); OC(O)R$_{11}$; N(R$_{11}$)C(O)R$_{11a}$; N(R$_{11}$)S(O)$_2R_{11a}$; N(R$_{11}$)S(O)R$_{11a}$; N(R$_{11}$)C(O)N(R$_{11a}R_{11}$); N(R$_{11}$)C(O)OR$_{11a}$; OC(O)N(R$_{11}R_{11a}$); oxo (=O), where the ring is at least partially saturated; C(O)R$_{11}$; $C_{1-6}$ alkyl; phenyl; $C_{3-7}$ cycloalkyl; or 5 or 6 membered saturated, unsaturated or aromatic heterocyclyl comprising at least one heteroatom selected from N, S and O; wherein $C_{1-6}$ alkyl, phenyl, $C_{3-7}$ cycloalkyl, and heterocyclyl are optionally substituted with one or more $R_{10}$;

$R_{10}$ is independently halogen; CN; OR$_{11}$; S(O)$_2$N(R$_{11}R_{11a}$); S(O)N(R$_{11}R_{11a}$); S(O)$_2R_{11}$; N(R$_{11}$)S(O)$_2$N(R$_{11a}R_{11b}$); SR$_{11}$; N(R$_{11}R_{11a}$); OC(O)R$_{11}$; N(R$_{11}$)C(O)R$_{11a}$; N(R$_{11}$)S(O)$_2R_{11a}$; N(R$_{11}$)S(O)R$_{11a}$; N(R$_{11}$)C(O)N(R$_{11a}R_{11b}$); N(R$_{11}$)C(O)OR$_{11a}$; OC(O)N(R$_{11}R_{11a}$); oxo (=O), where the ring is at least partially saturated; C(O)R$_{11}$; $C_{1-6}$ alkyl; phenyl; $C_{3-7}$ cycloalkyl; or heterocyclyl;

$R_{11}$, $R_{11a}$, $R_{11b}$ are independently selected from the group consisting of hydrogen, $C_{1-6}$ alkyl, $C_{1-6}$ alkyl $C_{3-10}$ cycloalkyl, $C_{3-10}$ cycloalkyl, $C_{1-6}$ alkyl 3 to 10 membered heterocycloalkyl comprising at least one heteroatom selected from N, S and O, 3 to 10 membered heterocycloalkyl comprising at least one heteroatom selected from N, S and O, $C_{6-10}$ aryl, 5 to 10 membered heteroaryl comprising at least one heteroatom selected from N, S and O, wherein $R_{11}$, $R_{11a}$, $R_{11b}$ are optionally substituted with one or more $R_9$;

or a metabolite, prodrug or a pharmaceutically acceptable salt thereof, wherein

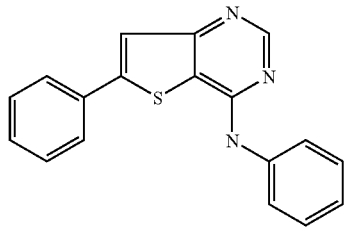 [SMILES: c1ccc(Nc2ncnc3cc(-c4ccccc4)sc23)cc1]

is excluded.

In a preferred embodiment, X is O, S, $SO_2$, $CH_2$, $CHR_{1a}$, $CR_{1a}R_{1b}$, CH(halogen), C(halogen)$_2$, C=O, C(O)$NR_{1a}$, NH or $NR_{1a}$, wherein $R_{1a}$ and $R_{1b}$ are $C_{1-6}$ alkyl, $C_{1-6}$ alkyl $C_{3-10}$ cycloalkyl, $C_{3-10}$ cycloalkyl, $C_{1-16}$ alkyl 3 to 10 membered heterocycloalkyl comprising at least one heteroatom selected from N, S and O, 3 to 10 membered heterocycloalkyl comprising at least one heteroatom selected from N, S and O, wherein $R_{1a}$ and $R_{1b}$ are optionally substituted with one or more $R_9$. Compounds in which X is a single bond, O or $NR_{1a}$ are more preferred. In a particularly preferred embodiment, X is O or $NR_{1a}$, even more preferably O.

In a preferred embodiment, $R_1$ is $C_{1-6}$ alkyl, $C_{1-6}$ alkyl $C_{3-10}$ cycloalkyl, $C_{3-10}$ cycloalkyl, $C_{1-6}$ alkyl 3 to 10 membered heterocycloalkyl comprising at least one heteroatom selected from N, S and O, 3 to 10 membered heterocycloalkyl comprising at least one heteroatom selected from N, S and O, $C_{6-10}$ aryl, $C_{1-6}$ alkyl $C_{6-10}$ aryl, $C_{5-10}$ heteroaryl comprising at least one heteroatom selected from N, S and O, $C_{1-6}$ alkyl $C_{5-10}$ heteroaryl comprising at least one heteroatom selected from N, S and O; wherein $R_1$ is optionally substituted with one or more $R_9$. Moreover, compounds as defined above, wherein $R_1$ is $C_{1-6}$ alkyl optionally substituted with one or more halogen atoms, $C_{3-10}$ cycloalkyl, a 3 to 10 membered heterocycloalkyl comprising a heteroatom selected from O and N and optionally being substituted with one or more $R_9$; or if X is $NR_{1a}R_1$ may form a 5 or 6 membered saturated, unsaturated or aromatic heterocyclic ring with $R_{1a}$ and the N atom to which they are attached are more preferred.

Also preferred are compounds, wherein $R_2$ and $R_3$ are independently selected from hydrogen, $C_{1-6}$ alkyl and $C_{6-10}$ aryl. More preferably, $R_2$ and $R_3$ are independently selected from hydrogen and $C_{1-6}$ alkyl, even more preferably from hydrogen and $CH_3$. In a particularly preferred embodiment, $R_2$ and $R_3$ are hydrogen.

Compounds wherein $R_4$ is hydrogen are preferred.

Compounds wherein $R_5$ is selected from hydrogen and halogen are preferred. Compounds wherein $R_5$ is hydrogen are particularly preferred.

The present invention also relates to compounds, wherein $R_6$ is selected from hydrogen, halogen, —C(O)N($R_{11}R_{11a}$), —$COOR_{11}$, and a 5 or 6 membered saturated, unsaturated or aromatic heterocyclic ring comprising at least one a heteroatom selected from N, S, and O, or together with $R_7$ forms a 5 or 6 membered saturated, unsaturated or aromatic heterocyclic ring comprising at least one a heteroatom selected from N, S, and O.

In a preferred embodiment, $R_6$ is selected from hydrogen, halogen, —C(O)N($R_{11}R_{11a}$), and —$COOR_{11}$.

Compounds wherein $R_7$ is hydrogen or together with $R_6$ forms a 5 or 6 membered saturated, unsaturated or aromatic heterocyclic ring comprising at least one a heteroatom selected from N, S, and O are preferred. In a preferred embodiment, $R_7$ is hydrogen.

Compounds wherein $R_8$ is hydrogen are preferred.

In one aspect, the present invention relates to compounds wherein $R_5$, $R_7$ and $R_8$ are hydrogen and, in another aspect, to compounds wherein $R_5$, $R_7$ and $R_8$ are hydrogen and $R_6$ is selected from fluorine, COOH and C(O)$NH_2$.

In another aspect, the present invention relates to compounds wherein $R_6$ together with $R_7$ forms a 5 or 6 membered saturated, unsaturated or aromatic heterocyclic ring comprising at least one, preferably two, heteroatoms selected from N, S, and O, preferably N.

The compounds of the present invention may contain a halogen atom preferable selected from Cl, Br and F.

Particularly preferred compounds are selected from:

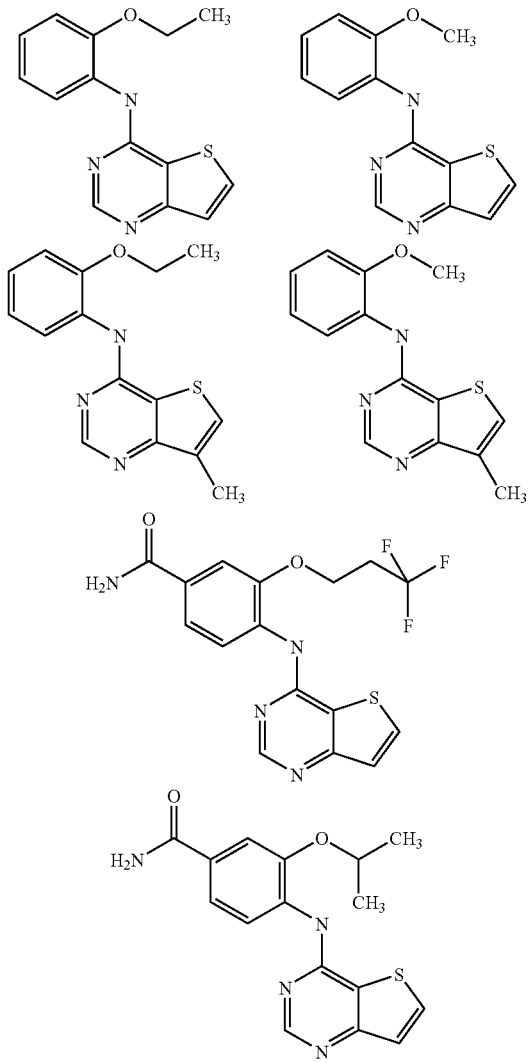

-continued
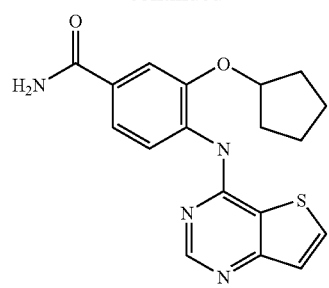
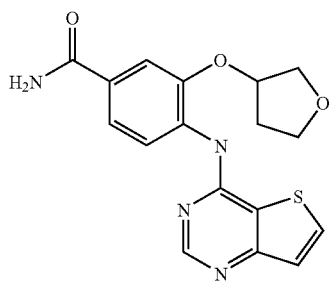 [SMILES: NC(=O)c1ccc(Nc2ncnc3ccsc23)c(OC2CCOC2)c1]
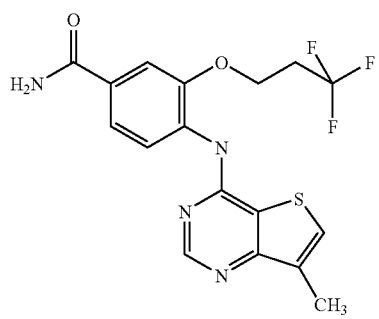
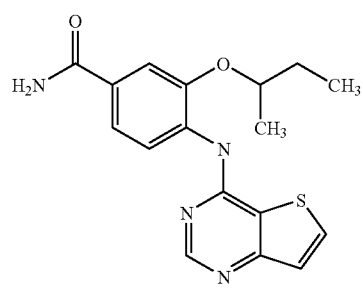
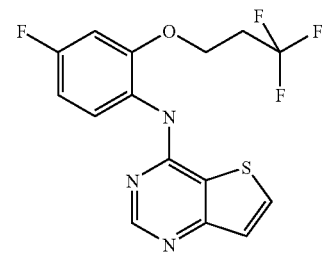
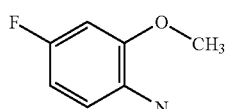
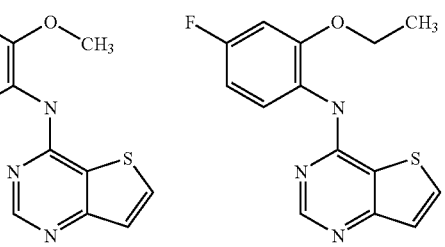
-continued
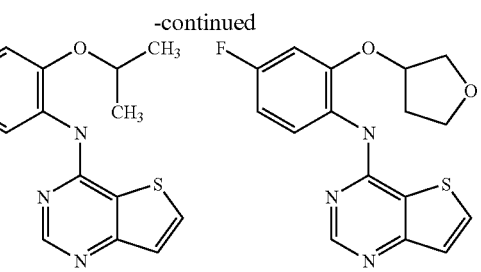
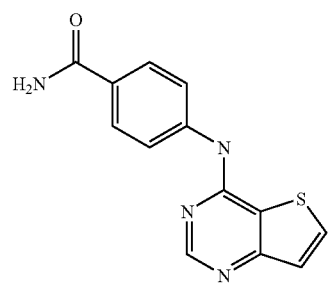
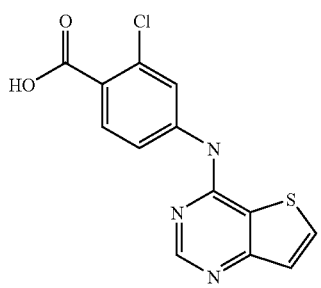
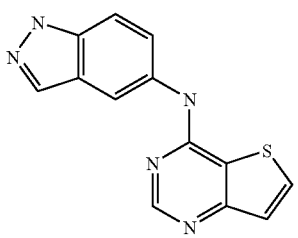
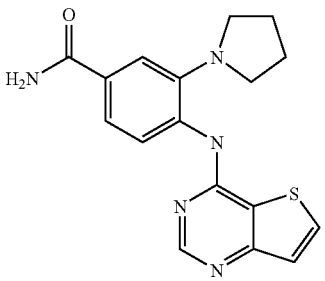
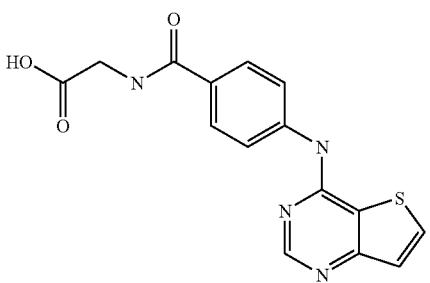

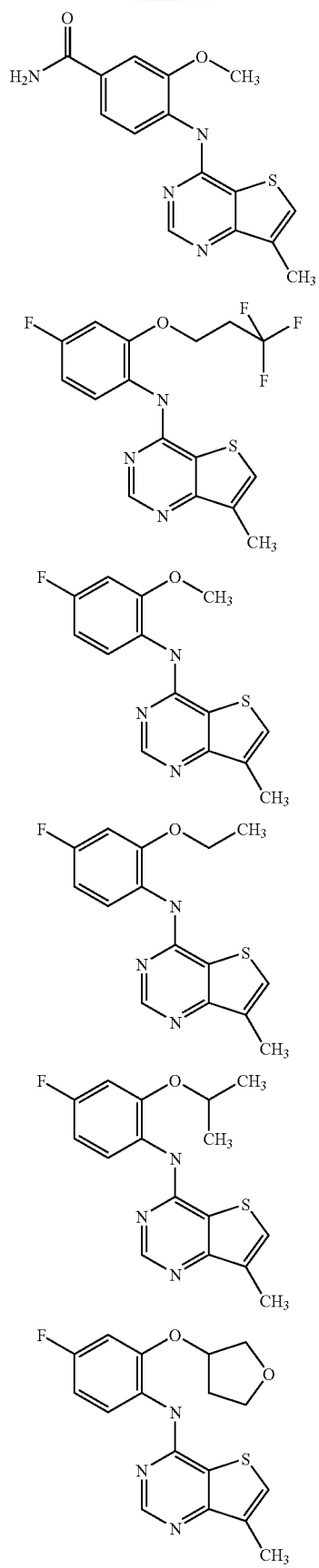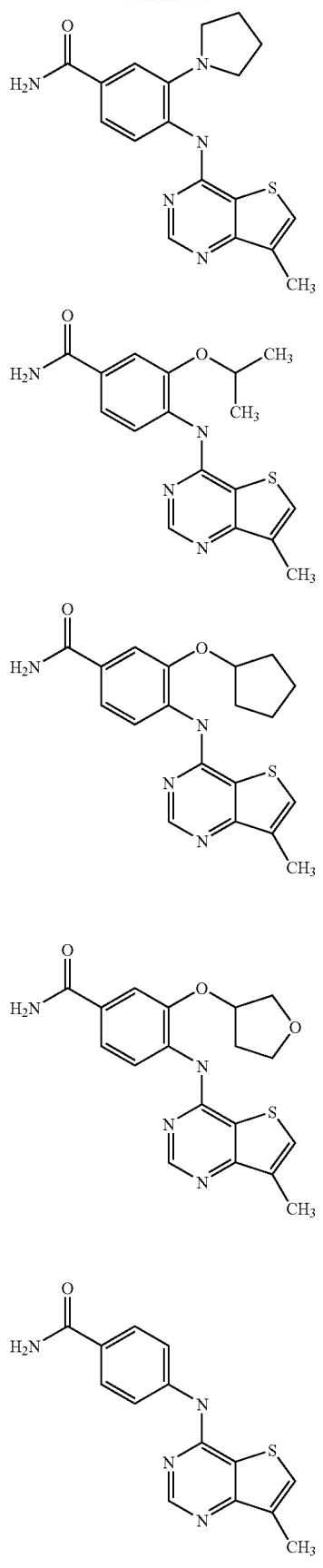

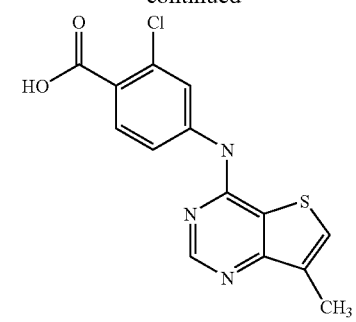
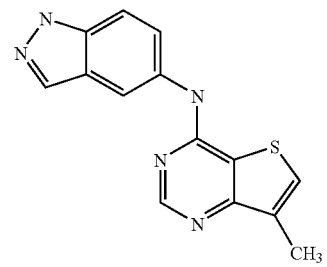
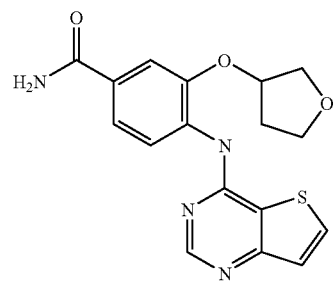
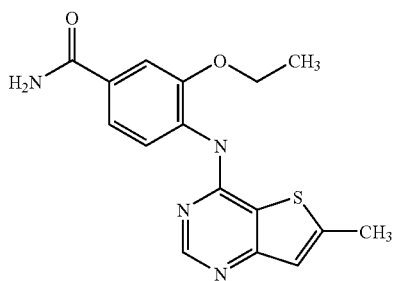
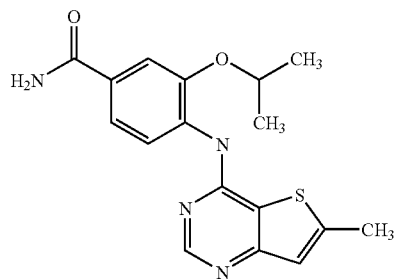
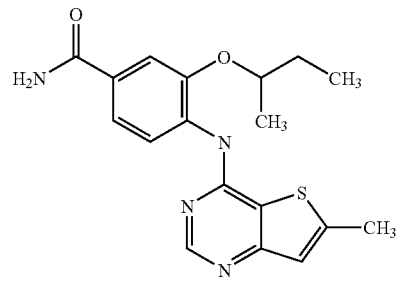
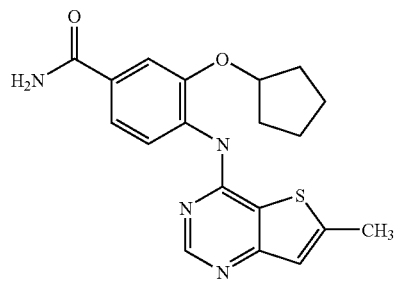
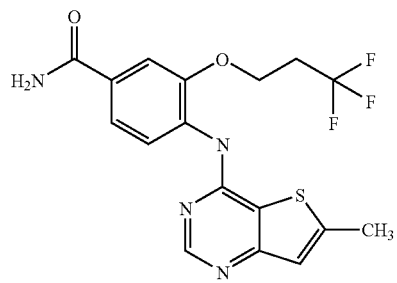
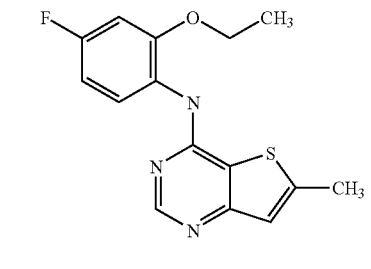
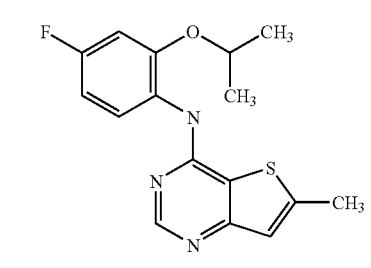
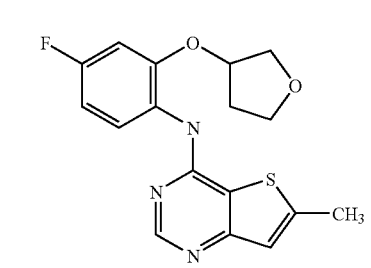
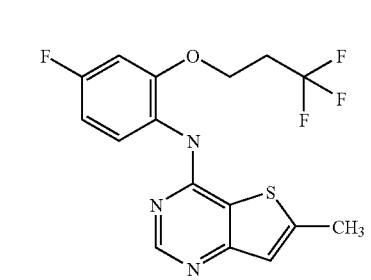

-continued
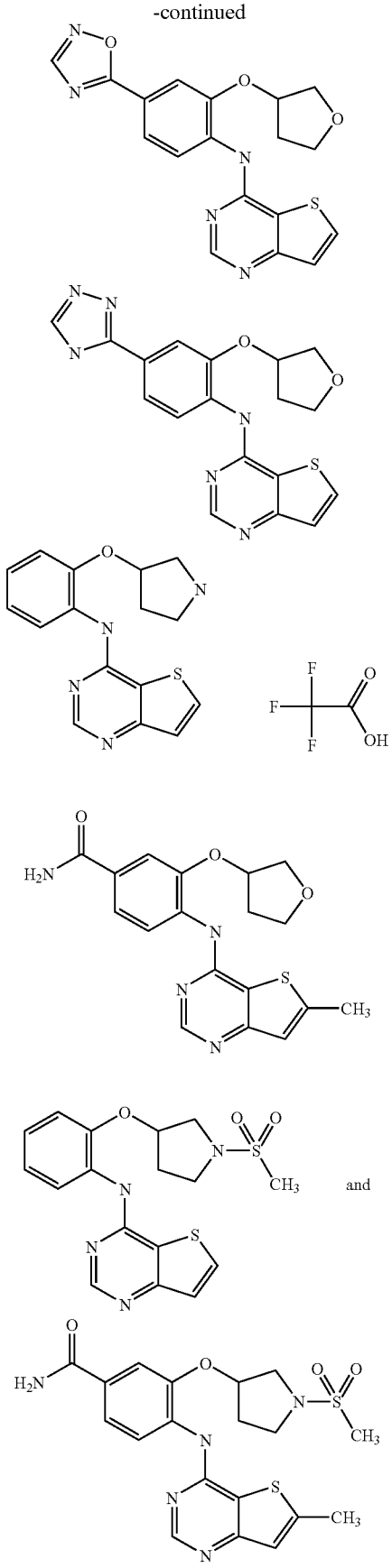
The following compounds are particularly preferred
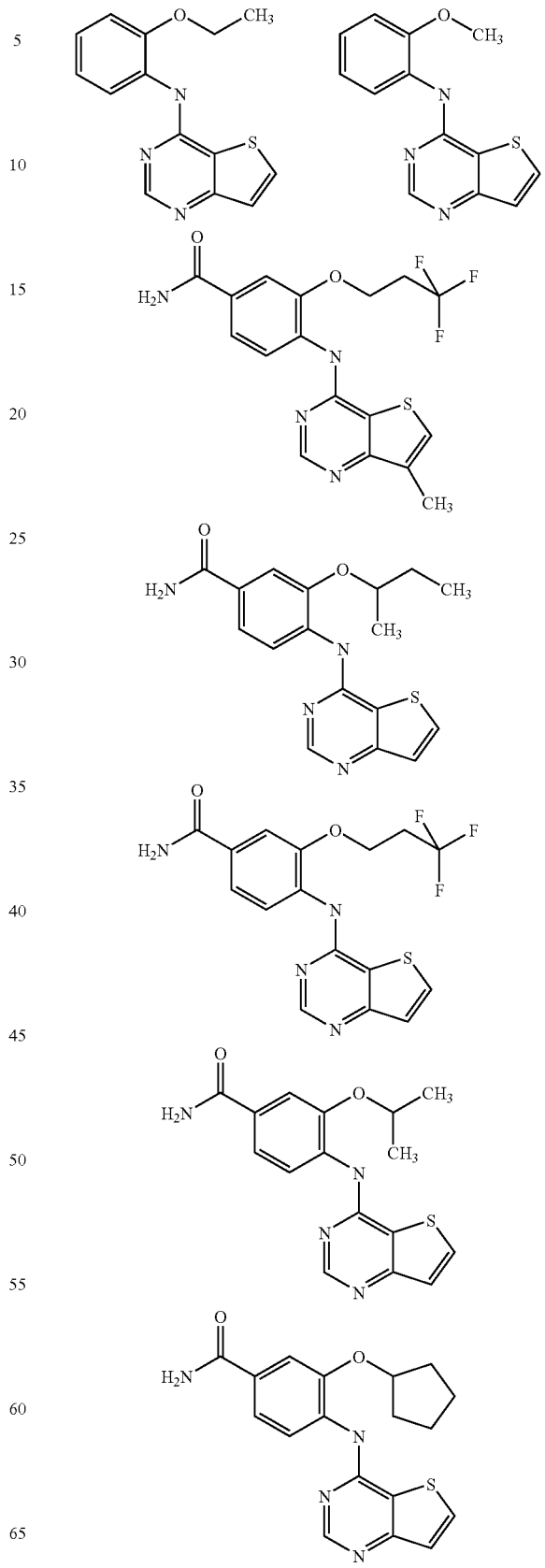

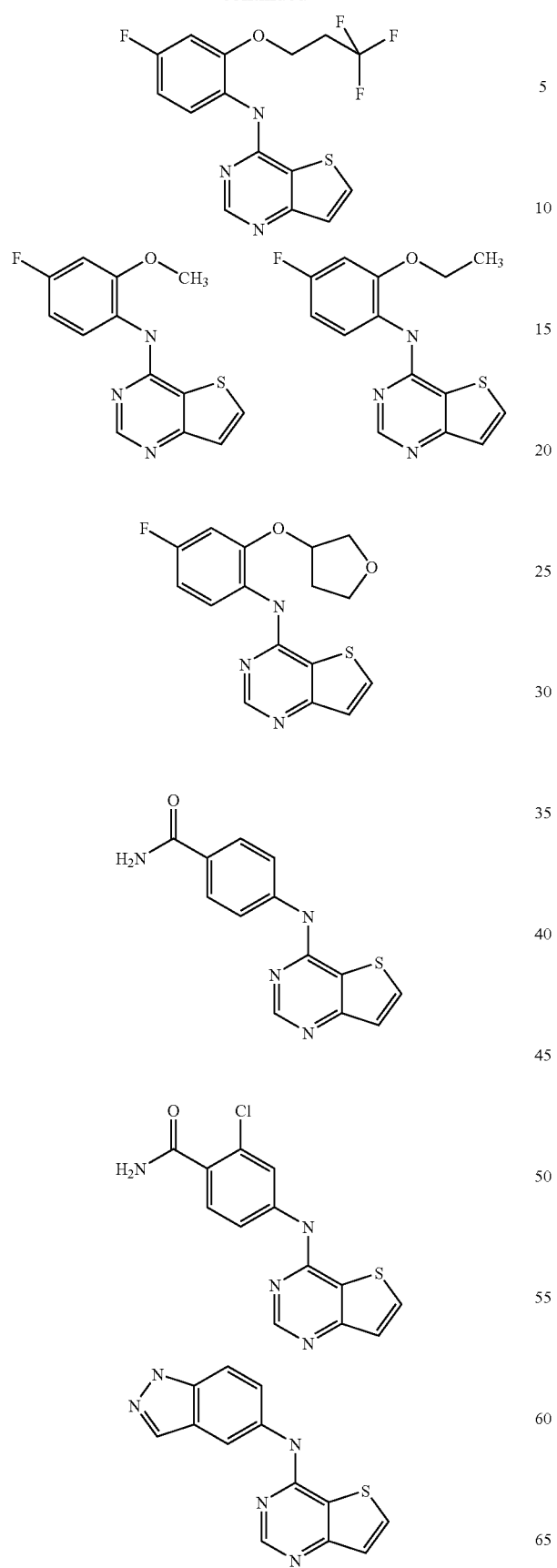
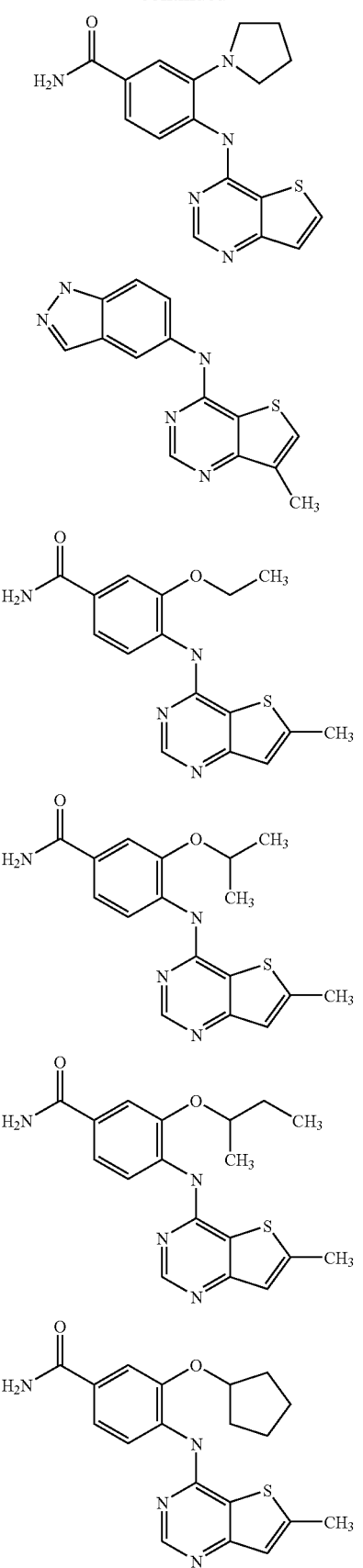

-continued

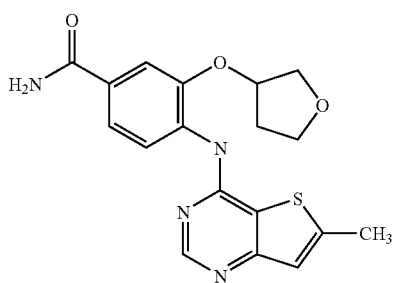
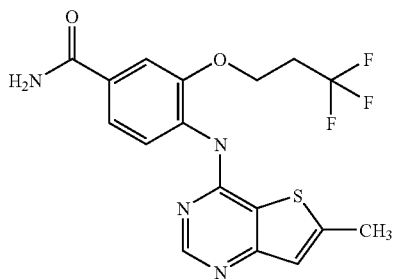
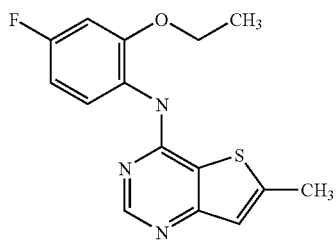
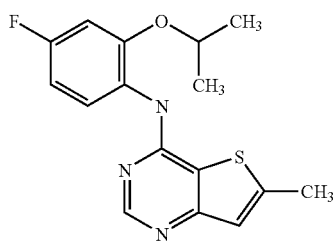
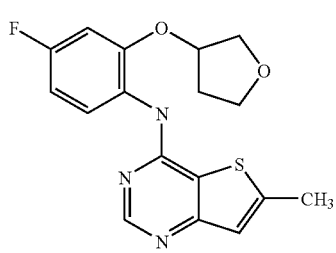
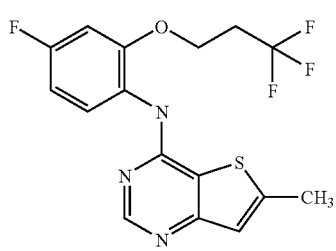

-continued

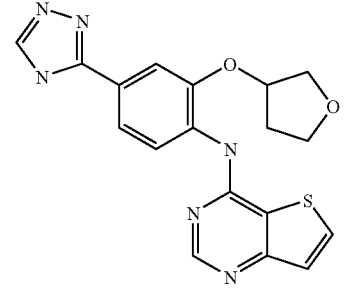
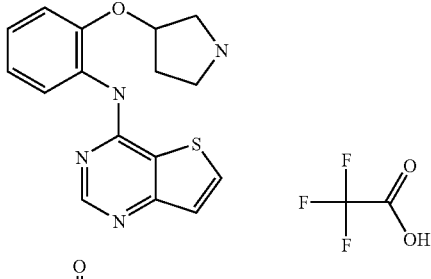
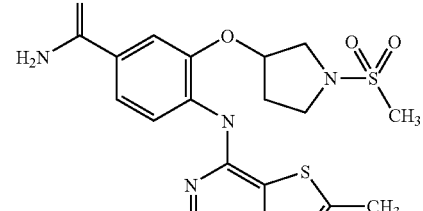
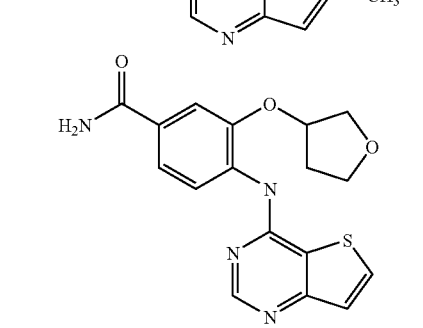

The following compound is more particularly preferred

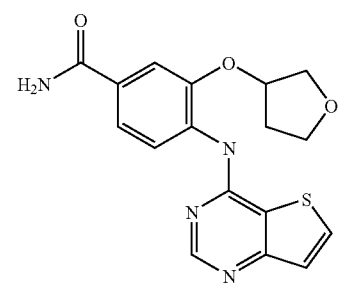 [SMILES: NC(=O)c1ccc(Nc2ncnc3ccsc23)c(OC2CCOC2)c1]

Typical methods of preparing the compounds of the invention are described below in the experimental section.

The potent inhibitory effect of the compounds of the invention may be determined by in vitro enzyme assays as described in the Examples in more detail.

Pharmaceutically acceptable salts of the compounds of the invention of formula (1) can be formed with numerous organic and inorganic acids and bases. Exemplary acid addition salts including acetate, adipate, alginate, ascorbate, aspartate, benzoate, benzenesulfonate, bisulfate, borate, butyrate, citrate, camphorate, camphersulfonate; cyclopentanepropionate, digluconate, dodecyl sulfate, ethane sulfonate, fumarate, glucoheptanoate, glycerophosphate, hemisulfate, heptanoate, hexanoate, hydrochloride, hydrobromide, hydroiodide, 2-hydroxyethane sulfonate, lactate, maleate, methane sulfonate, 2-naphthalene sulfonate, nicotinate, nitrate, oxalate, pamoate, pectinate, persulfate, 3-phenyl sulfonate, 3-phenylpropionate, phosphate, picrate, pivalate, propionate, salicylate, succinate, sulfate, sulfonate, tartrate, thiocyanate, toluene sulfonate such as tosylate, undecanoate, or the like.

Basic nitrogen-containing moieties can be quaternized with such agents as lower alkyl halides, such as methyl, ethyl, propyl, and butyl chloride, bromide and iodide; dialkyl sulfates like dimethyl, diethyl, dibutyl, and diamyl sulfates, long-chain alkyl halides such as decyl, lauryl, myristyl and stearyl chloride, bromide and iodide, or aralkyl halides like benzyl and phenethyl bromides, or others. Water soluble or dispersible products are thereby obtained.

Pharmaceutically acceptable basic addition salts include but are not limited to cations based on the alkaline and alkaline earth metals such as sodium, lithium, potassium, calcium, magnesium, aluminum salts and the like, as well as non toxic ammonium quarternary ammonium, and amine cations, including but not limited to ammonium, tetramethylammonium, tetraethylammonium, methylamine, dimethylamine, trimethylamine, triethylamine, ethylamine and the like. Other representative amines useful for the formation of base addition salts include benzazethine, dicyclohexyl amine, hydrabine, N-methyl-D-glucamine, N-methyl-D-glucamide, t-butyl amine, diethylamine, ethylendiamine, ethanolamine, diethanolamine, piperazine and the like and salts with amino acids such as arginine, lysine, or the like.

Compounds of the formula (1) can be present as tautomers. The present invention comprises all tautomeric forms. Furthermore, the present invention also comprises all stereoisomers of the compounds according to the invention, including its enantiomers and diastereomers. Individual stereoisomers of the compounds according to the invention can be substantially present pure of other isomers, in admixture thereof or as racemates or as selected stereoisomers.

As used herein the term "metabolite" refers to (i) a product of metabolism, including intermediate and products, (ii) any substance involved in metabolism (either as a product of metabolism or as necessary for metabolism), or (iii) any substance produced or used during metabolism. In particular it refers to the end product that remains after metabolism.

As used herein the term "prodrug" refers to (i) an inactive form of a drug that exerts its effects after metabolic processes within the body convert it to a usable or active form, or (ii) a substance that gives rise to a pharmacologically active metabolite, although not itself active (i.e. an inactive precursor).

As used herein the term "$C_{3-10}$ cycloalkyl" refers to mono- or polycyclic carbocyclic alkyl substituent or group having 3 to 10 ring atoms, such as cyclopropyl, cyclobutyl, cyclopentyl, cyclohexyl, cycloheptyl, cyclobutenyl, cyclopentenyl, cyclopentadienyl, cyclohexenyl, cyclohexadienyl, cycloheptenyl, cycloheptadienyl, cycloheptatrienyl perhydrated naphthalene or indene, adamantyl or norbonanyl and the like.

The term "$C_{1-6}$ alkyl" as used herein alone or in combination with other terms such as in alkoxy refers to a $C_{1-6}$, preferably $C_{1-4}$ straight or branched alkyl/alkoxy group such as methyl, ethyl, propyl (iso-, n-), butyl (iso-, n-, sec-, tert-), pentyl, hexyl, methoxy, ethoxy, propoxy (iso-, n-), butoxy (iso-, n-, sec-, tert-), pentoxy, hexoxy; moreover, the term "$C_{1-6}$ alkyl" also includes an alkyl group which may contain oxygen in the chain and may be substituted with halogen to form an ether or halogenated ether group.

The term "halogen" refers to a halogen atom selected from fluorine, chlorine, bromine, iodine, preferably fluorine and chlorine, more preferably fluorine.

The term "aryl" refers to a mono- or bicyclic aromatic group having 6 to 10 backbone carbon atoms, wherein optionally one of the rings of the bicyclic structure is aromatic and the other is a carbocyclic group, such as phenyl, 1-naphthyl, 2-naphthyl, indenyl, indanyl, azulenyl, fluorenyl, 1,2,3,4-tetrahydronaphthyl.

The term "heterocyclyl" refers to monocyclic saturated or unsaturated heterocyclyl groups with 1 to 4 hetero atoms selected from N, S and O, with the remainder of the ring atoms being carbon atoms and having preferably a total number of ring atoms of 3 to 10, such as morpholino, piperazinyl, piperidinyl, pyridyl, pyrimidinyl, thiazolyl, indolyl, imidazolyl, oxadiazolyl, tetrazolyl, pyrazinyl, triazolyl, thiophenyl or furanyl.

The term "heteroaryl" refers to a mono- or bicyclic aromatic group with 1 to 4 hetero atoms selected from N, S and O, with the remainder of the ring atoms being carbon atoms and having preferably a total number of ring atoms of 5 to 10. Examples without limitation of heteroaryl groups are such as benzofuranyl, furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, quinolinyl, isoquinolinyl, purinyl, carbazolyl, benzoxazolyl, benzamidazolyl, indolyl, isoindolyl, pyrazinyl, diazinyl, pyrazine, triazinyltriazine, tetrazinyl, tetrazolyl, benzothiophenyl, benzopyridyl and benzimidazolyl.

In a further aspect the present invention provides pharmaceutical compositions comprising a thienopyrimidine compound of the present invention and optionally a pharmaceutically acceptable carrier.

The pharmaceutical composition according to the present invention may further comprise an additional therapeutic agent. Particularly preferred are compositions, wherein the additional therapeutic agent is selected from antidiabetics like insulin, long and short acting insulin analogues, sulfonylureas and other antidiabetics derived from thiazolidindiones, lipid lowering agents such as statines, fibrates, ion exchange resins, nicotinic acid derivatives, or HMG-CoA reductase inhibitors, cardiovascular therapeutics such as nitrates, antihypertensiva such as β-blockers, ACE inhibitors, Ca-channel blockers, angiotensin II receptor antagonists, diuretics, thrombocyte aggregation inhibitors, or antineoplastic agents such as alkaloids, alkylating agents, antibiotics, or antimetabolites, or anti-obesity agents. Further preferred compositions are compositions wherein the additional therapeutic agent is selected from a histamine antagonist, a bradikinin antagonist, serotonin antagonist, leukotriene, an anti-asthmatic, an NSAID, an antipyretic, a corticosteroid, an antibiotic, an analgetic, a uricosuric agent, chemotherapeutic agent, an anti gout agent, a bronchodilator, a cyclooxygenase-2 inhibitor, a steroid, a 5-lipoxygenase inhibitor, an immunosuppressive agent, a leukotriene antagonist, a cytostatic agent, antibodies or fragments thereof against cytokines and soluble parts (fragments) of cytokine receptors.

More particularly preferred are compounds such as human NPH insulin, human lente or ultralente insulin, insulin Lispro, insulin Asptart, or insulin Glargine, atenolol, bisoprolol, metoprolol, esmolol, celiprolol, talinolol, oxprenolol, pindolol, propanolol, bupropanolol, penbutolol, mepindolol, sotalol, certeolol, nadolol, carvedilol, nifedipin, nitrendipin, amlodipin, nicardipin, nisoldipin, diltiazem, enalapril, verapamil, gallopamil, quinapril, captopril, lisinopril, benazepril, ramipril, peridopril, fosinopril, trandolapril, irbesatan, losartan, valsartan, telmisartan, eprosartan, olmesartan, hydrochlorothiazide, piretanid, chlorotalidone, mefruside, furosemide, bendroflumethiazid, triamterene, dehydralazine, acetylsalicylic acid, tirofiban-HCl, dipyramidol, triclopidin, iloprost-trometanol, eptifibatide, clopidogrel, piratecam, abciximab, trapidil, simvastatine, bezafibrate, fenofibrate, gemfibrozil, etofyllin, clofibrate, etofibrate, fluvastatine, lovastatine, pravastatin, colestyramide, colestipol-HCl, xantinol nicotinat, inositol nicotinat, acipimox, nebivolol, glycerolnitrate, isosorbide mononitrate, isosorbide dinitrate, pentaerythrityl tetranitrate, indapamide, cilazepril, urapidil, eprosartan, nilvadipin, metoprolol, doxazosin, molsidormin, moxaverin, acebutolol, prazosine, trapidil, clonidine, vinca alkaloids and analogues such as vinblastin, vincristin, vindesin, vinorelbin, podophyllotoxine derivatives, etoposid, teniposid, alkylating agents, nitroso ureas, N-lost analogues, cycloplonphamid, estamustin, melphalan, ifosfamid, mitoxantron, idarubicin, doxorubicin, bleomycin, mitomycin, dactinomycin, daptomycin, antimetabolites such as cytarabin, fluorouracil, fluoroarabin, gemcitabin, tioguanin, capecitabin, combinations such as adriamycin/daunorubicin, cytosine arabinosid/cytarabine, 4-HC, or other phosphamides.

Other particularly preferred compounds are compounds such as clemastine, diphenhydramine, dimenhydrinate, promethazine, cetirizine, astemizole, levocabastine, loratidine, terfenadine, acetylsalicylic acid, sodoum salicylate, salsalate, diflunisal, salicylsalicylic acid, mesalazine, sulfasalazine, osalazine, acetaminophen, indomethacin, sulindac, etodolac, tolmetin, ketorolac, bethamethason, budesonide, chromoglycinic acid, dimeticone, simeticone, domperidone, metoclopramid, acemetacine, oxaceprol, ibuprofen, naproxen, ketoprofen, flubriprofen, fenoprofen, oxaprozin, mefenamic acid, meclofenamic acid, pheylbutazone, oxyphenbutazone, azapropazone, nimesulide, metamizole, leflunamide, eforicoxib, lonazolac, misoprostol, paracetamol, aceclofenac, valdecoxib, parecoxib, celecoxib, propyphenazon, codein, oxapozin, dapson, prednisone, prednisolon, triamcinolone, dexibuprofen, dexamethasone, flunisolide, albuterol, salmeterol, terbutalin, theophylline, caffeine, naproxen, glucosamine sulfate, etanercept, ketoprofen, adalimumab, hyaluronic acid, indometacine, proglumetacine dimaleate, hydroxychloroquine, chloroquine, infliximab, etofenamate, auranofin, gold, [$^{224}$Ra]radium chloride, tiaprofenic acid, dexketoprofen(trometamol), cloprednol, sodium aurothiomalate aurothioglucose, colchicine, allopurinol, probenecid, sulfinpyrazone, benzbromarone, carbamazepine, lornoxicam, fluorcortolon, diclofenac, efalizumab, idarubicin, doxorubicin, bleomycin, mitomycin, dactinomycin, daptomycin, cytarabin, fluorouracil, fluoroarabin, gemcitabin, tioguanin, capecitabin, adriamydin/daunorubicin, cytosine arabinosid/cytarabine, 4-HC, or other phosphamides, penicillamine, a hyaluronic acid preparation, arteparon, glucosamine, MTX, soluble fragments of the TNF-receptor (such as etanercept (Enbrel)) and antibodies against TNF (such as infliximab (Remicade), natalizumab (Tysabri) and adalimumab (Humira)).

It will be appreciated by the person of ordinary skill in the art that the compounds of the invention and the additional therapeutic agent may be formulated in one single dosage form, or may be present in separate dosage forms and may be either administered concomitantly (i.e. at the same time) or sequentially.

The pharmaceutical compositions of the present invention may be in any form suitable for the intended method of administration.

The compounds of the present invention may be administered orally, parenterally, such as bronchopulmonary, subcutaneously, intravenously, intramuscularly, intraperitoneally, intrathecally, transdermally, transmucosally, subdurally, locally or topically via iontophoresis, sublingually, by inhalation spray, aerosol or rectally and the like in dosage unit formulations optionally comprising conventional pharmaceutically acceptable excipients.

Excipients that may be used in the formulation of the pharmaceutical compositions of the present invention comprise carriers, vehicles, diluents, solvents such as monohydric alcohols such as ethanol, isopropanol and polyhydric alcohols such as glycols and edible oils such as soybean oil, coconut oil, olive oil, safflower oil cottonseed oil, oily esters such as ethyl oleate, isopropyl myristate; binders, adjuvants, solubilizers, thickening agents, stabilizers, disintergrants, glidants, lubricating agents, buffering agents, emulsifiers, wetting agents, suspending agents, sweetening agents, colorants, flavors, coating agents, preservatives, antioxidants, processing agents, drug delivery modifiers and enhancers such as calcium phosphate, magnesium state, talc, monosaccharides, disaccharides, starch, gelatine, cellulose, methylcellulose, sodium carboxymethyl cellulose, dextrose, hydroxypropyl-β-cyclodextrin, polyvinylpyrrolidone, low melting waxes, ion exchange resins.

Other suitable pharmaceutically acceptable excipients are described in Remington's Pharmaceutical Sciences, 15$^{th}$ Ed., Mack Publishing Co., New Jersey (1991).

Dosage forms for oral administration include tablets, capsules, lozenges, pills, wafers, granules, oral liquids such as syrups, suspensions, solutions, emulsions, powder for reconstitution.

Dosage forms for parenteral administration include aqueous or olageous solutions or emulsions for infusion, aqueous or olageous solutions, suspensions or emulsions for injection pre-filled syringes, and/or powders for reconstitution. Dosage forms for local/topical administration comprise insufflations, aerosols, metered aerosols, transdermal therapeutic systems, medicated patches, rectal suppositories, and/or ovula.

The amount of the compound of the present invention that may be combined with the excipients to formulate a single dosage form will vary upon the host treated and the particular mode of administration.

The pharmaceutical compositions of the invention can be produced in a manner known per se to the skilled person as described, for example, in Remington's Pharmaceutical Sciences, 15$^{th}$ Ed., Mack Publishing Co., New Jersey (1991).

In a further aspect of the invention the use of a thienopyrimidine compound of the present invention for the production of a pharmaceutical composition for inhibiting the activity of the kinase activity of Mnk1 or Mnk2 (Mnk2a, Mnk2b) or further variants thereof is provided, in particular for the prophylaxis or therapy of metabolic diseases, hematopoietic disorders, cancer and their consecutive complications and disorders. Whereby the prophylaxis and therapy of metabolic diseases of the carbohydrate and/or lipid metabolism is preferred.

Diseases of the invention that are influenced by the inhibition of the kinase activity of Mnk1 and/or Mnk2 (Mnk2a or Mnk2b) and/or further variants thereof include diseases related to the regulation of metabolic diseases, such as obesity, eating disorders, cachexia, diabetes mellitus, metabolic syndrome, hypertension, coronary heart diseases, hypercholesterolemia, dyslipidemia, osteoarthritis, biliary stones and/ or sleep apnea and diseases related to reactive oxygen compounds (ROS defense) such as diabetes mellitus, neurodegenerative diseases and cancer.

The pharmaceutical compositions of the invention are particularly useful for prophylaxis and treatment of obesity, diabetes mellitus and other metabolic diseases of the carbohydrate and lipid metabolism as stated above, in particular diabetes mellitus and obesity.

Thus in a more preferred embodiment of this invention the use of a thienopyrimidine compound for the production of a pharmaceutical composition for the prophylaxis or therapy of metabolic diseases is provided.

In yet a further aspect of the invention the use of a thienopyrimidine compound of the invention for the production of a pharmaceutical composition for treating or preventing a cytokine mediated disorder such as an inflammatory disease.

The pharmaceutical compositions of the invention are thus useful for the prophylaxis or therapy of inflammatory diseases, in particular chronic or acute inflammation, chronic inflammatory arthritis, rheumatoid arthritis, psoriatic arthritis, osteoarthritis, juvenile rheumatoid arthritis, gouty arthritis; psoriasis, erythrodermic psoriasis, pustular psoriasis, inflammatory bowel disease, Crohn's disease and related conditions, ulcerative colitis, colitis, diverticulitis, nephritis, urethritis, salpingitis, oophoritis, endomyometritis, spondylitis, systemic lupus erythematosus and related disorders, multiple sclerosis, asthma, meningitis, myelitis, encephalomyelitis, encephalitis, phlebitis, thrombophlebitis, chronic obstructive disease (COPD), inflammatory lung disease, allergic rhinitis, endocarditis, osteomyelitis, rheumatic fever, rheumatic pericarditis, rheumatic endocarditis, rheumatic myocarditis, rheumatic mitral valve disease, rheumatic aortic valve disease, prostatitis, prostatocystitis, spondoarthropathies ankylosing spondylitis, synovitis, tenosynovotis, myositis, pharyngitis, polymyalgia rheumatica, shoulder tendonitis or bursitis, gout, pseudo gout, vasculitides, inflammatory diseases of the thyroid selected from granulomatous thyroiditis, lymphocytic thyroiditis, invasive fibrous thyroiditis, acute thyrbiditis; Hashimoto's thyroiditis, Kawasaki's disease, Raynaud's phenomenon, Sjogren's syndrome, neuroinflammatory disease, sepsis, conjubctivitis, keratitis, iridocyclitis, optic neuritis, otitis, lymphoadenitis, nasopaharingitis, sinusitis, pharyngitis, tonsillitis, laryngitis, epiglottitis, bronchitis, pneumonitis, stomatitis, gingivitis, oesophagitis, gastritis, peritonitis, hepatitis, cholelithiasis, cholecystitis, glomerulonephritis, goodpasture's disease, crescentic glomerulonephritis, pancreatitis, dermatitis, endomyometritis, myometritis, metritis, cervicitis, endocervicitis, exocervicitis, parametritis, tuberculosis, vaginitis, vulvitis, silicosis, sarcoidosis, pneumoconiosis, inflammatory polyarthropathies, psoriatric arthropathies, intestinal fibrosis, bronchiectasis and enteropathic arthropathies.

As already stated above, the compositions of the present invention are particularly useful for treating or preventing a disease selected from chronic or acute inflammation, chronic inflammatory arthritis, rheumatoid arthritis, psoriasis, COPD, inflammatory bowel disease, septic shock, Crohn's disease, ulcerative colitis, multiple sclerosis and asthma.

Thus, in a more preferred embodiment of this invention the use of a pyrazolopyrimidine compound for the production of a pharmaceutical composition for the prophylaxis or therapy of inflammatory diseases selected from chronic or acute inflammation, chronic inflammatory arthritis, rheumatoid arthritis, psoriasis, COPD, inflammatory bowel disease, septic shock Crohn's disease, ulcerative colitis, multiple sclerosis and asthma is provided.

For the purpose of the present invention, a therapeutically effective dosage will generally be from about 1 to 500 mg/day, preferably from about 10 to about 200 mg/day, and most preferably from about 10 to about 100 mg/day, which may be administered in one or multiple doses.

It will be appreciated, however, that specific dose level of the compounds of the invention for any particular patient will depend on a variety of factors such as age, sex, body weight, general health condition, diet, individual response of the patient to be treated time of administration, severity of the disease to be treated, the activity of particular compound applied, dosage form, mode of application and concomitant medication. The therapeutically effective amount for a given situation will readily be determined by routine experimentation and is within the skills and judgment of the ordinary clinician or physician.

EXAMPLES

Example 1

Examples of Preparation of the Compounds of the Invention

General Synthetic Methods for the Compounds of the Invention, their Derivatives and Precursors In the following several general synthetic methods are described.

Route A

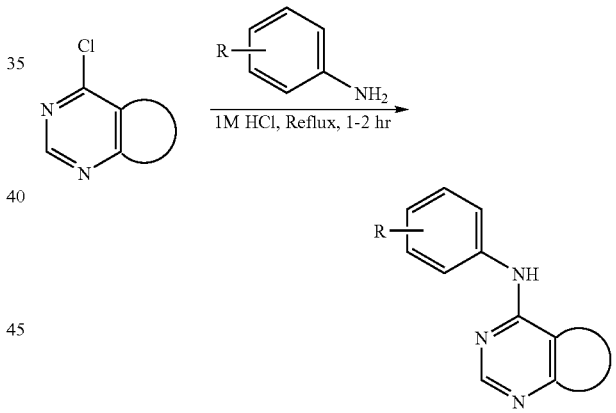

The amine (1.0 eq) and the 4-Cl-pyrimidine derivative (1.0 eq) were heated at reflux in aqueous 1 M HCl in a sealed tube for 1-2 hours. The reaction was then allowed to cool to room temperature, and basified to pH 9-10 with 28% ammonium hydroxide solution. The resultant precipitate was isolated by filtration, washed with water, dried on the sinter, washed with diethyl ether, and dried in vacuo to give the desired product.

- If the amine group contains an acid the reaction is not basified.
- The reactions are typically carried out on a 50 mg. scale in 1-2 ml of 1M HCl to give >10 mg product
- If the reaction does not yield a precipitate, solvent is removed and the solid is triturated with water to give the desired product.
- The pyrimidine derivative can be formed as a major by-product and can be removed by trituration from hot methanol Route B

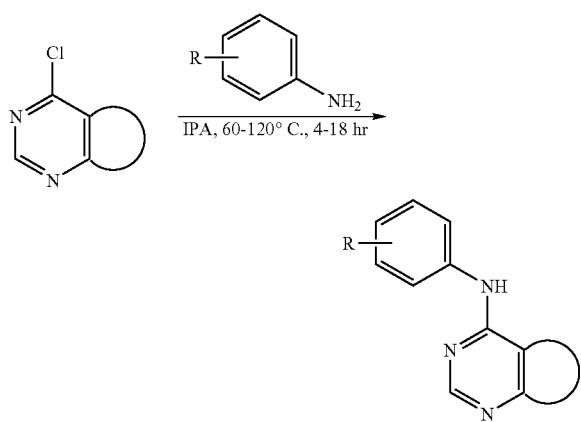

The amine (1.0 eq) and the 4-Cl-pyrimidne derivative (1.0 eq) were heated at 60° C. in IPA in a sealed tube for 4-18 hours. The reaction was then allowed to cool to room temperature, and basified to pH 9-10 with 28% ammonium hydroxide solution. The resultant precipitate was isolated by filtration, washed with water, dried on the sinter, washed with diethyl ether, and dried in vacuo to give the desired product.

If the amine group contains an acid the reaction is not basified.

The reactions are typically carried out on a 50 mg scale in 2-3 ml of IPA to give >10 mg product If the reaction does not yield a precipitate, solvent is removed and the solid is triturated with water to give the desired product.

The 5,6-substituted thienopyrimidines typically need longer reaction times and higher temperatures Transformation of Carboxylic Acids to Esters, Amides and Hydroxamic Acids For the scheme below the parent carboxylic acid was prepared via routes A or B.

Route C

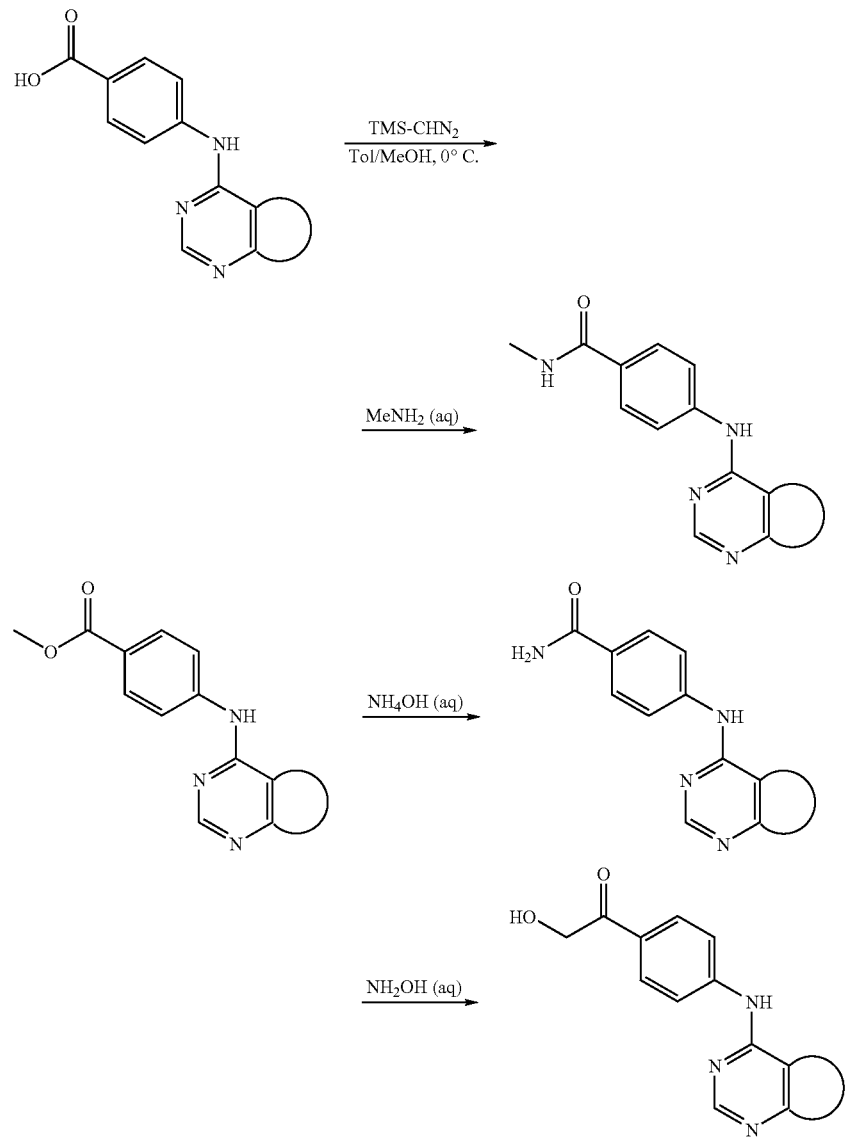

Methyl Ester Formation

The carboxylic acid (1.0 eq) was suspended in toluene/methanol [3:1] and cooled to 0° C. To this mixture TMS-diazomethane (2 M solution in Et$_2$O, 1.3 eq) was added dropwise. The reaction mixture was stirred for 30 minutes at 0° C. then allowed to warm to room temperature and stir until the reaction was complete. The solvent was removed in vacuo to give the desired product.

If the reaction was not complete after 3 hours a further equivalent of TMS-diazomethane (2 M solution in Et$_2$O) was added to the reaction mixture and stirring continued at room temperature until the reaction was complete.

Primary Carboxamide Formation

The starting methyl ester was suspended in 28% w/w NH$_4$OH solution (5-10 vol) in an ACE pressure tube and heated at 90° C. for 8 hours. The reaction mixture was allowed to cool to room temperature and the resultant precipitate isolated by filtration. The filter cake was washed with acetone, diethyl ether and dried to give the desired product.

If no precipitate was obtained, the solvent was removed in vacuo and the resultant solid purified via semi-preparative HPLC if required.

Methyl Carboxamide Formation

The starting methyl ester was suspended in 40% w/w methylamine solution (7 vol) in an ACE pressure tube. After heating at 80° C. for 18 hours the reaction mixture was allowed to cool to room temperature. The resultant precipitate was isolated by filtration and dried to give the desired product.

Hydroxylamine Formation

The starting methyl ester was suspended in 50% w/w aqueous hydroxylamine solution (7 vol) and stirred at room temperature for 18 hours. The solvent was then removed in vacuo and the resultant residue triturated with acetone. The resultant precipitate was collected via filtration, washed with DCM and dried to give the desired product.

Route K

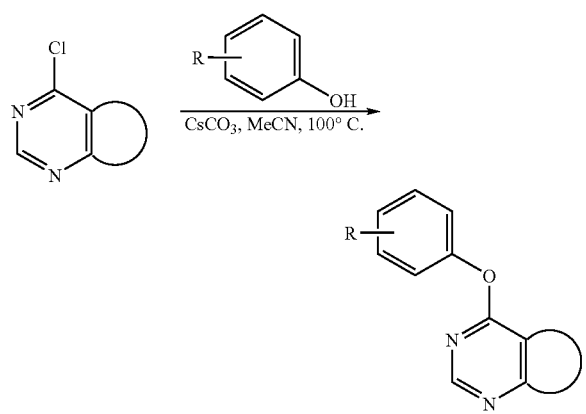

Caesium carbonate (0.6 eq), the phenol (1.0 eq) and the 4-Cl-pyrimidine derivative (1.0 eq) were charged to a sealed tube and suspended in acetonitrile (40 vol). The reaction was then heated at 100° C. for 18 hours before being allowed to cool and the inorganics removed by filtration. The solvent was removed in vacuo and the resultant residue purified by column chromatography.

Route L

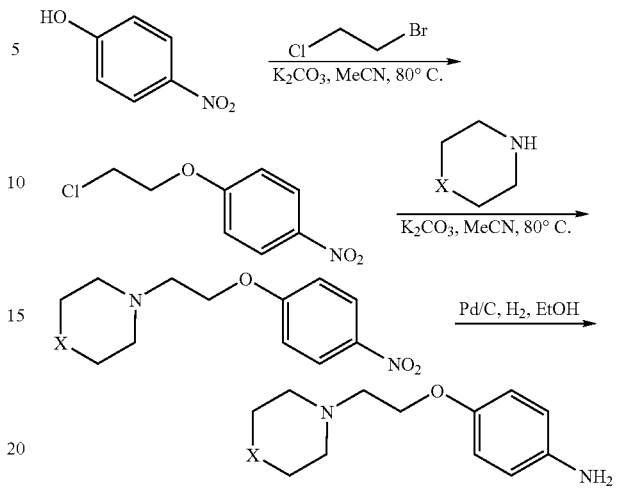

Alkylation of the Phenol

The nitro-phenol (1.0 eq) was dissolved in acetonitrile (10 vol) and potassium carbonate (2.0 eq) added. After stirring at room temperature for 10 minutes, 1-bromo-2-chloroethane (3.0 eq) was added and the reaction heated at 80° C. for 18 hours. The reaction mixture was then allowed to cool, the inorganics were removed by filtration and the solvent removed in vacuo. The resultant residue was taken on to the next step without purification.

Tertiary Amine Formation

The alkyl chloride (1.0 eq) was added to a suspension of potassium carbonate (2.0 eq) and amine (2.0 eq) in acetonitrile (10 vol). The reaction was the heated to 80° C. for 18 hours and then allowed to cool. The inorganics were then removed by filtration, the solvent removed in vacuo, and the resultant residue purified by flash column chromatography.

Hydrogenation

The aryl-nitro compound was dissolved in ethanol (5 vol) and 10% w/w Palladium on carbon (10% w/w) added. The mixture was then purged with N$_2$ twice, then placed under a H$_2$ atmosphere and left to stir for 18 hours. The reaction was then purged with N$_2$ twice and the palladium residues removed by filtration through a celite pad. The solvent was then removed in vacuo and the desired aniline then taken forward without any further purification.

Route N

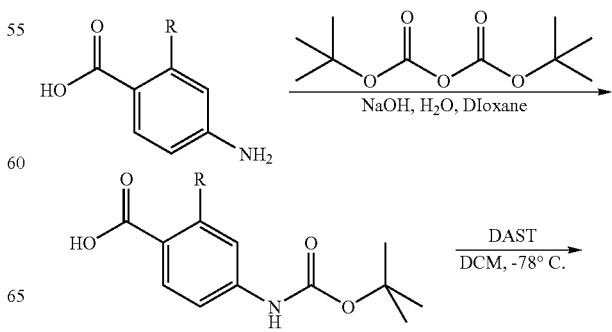

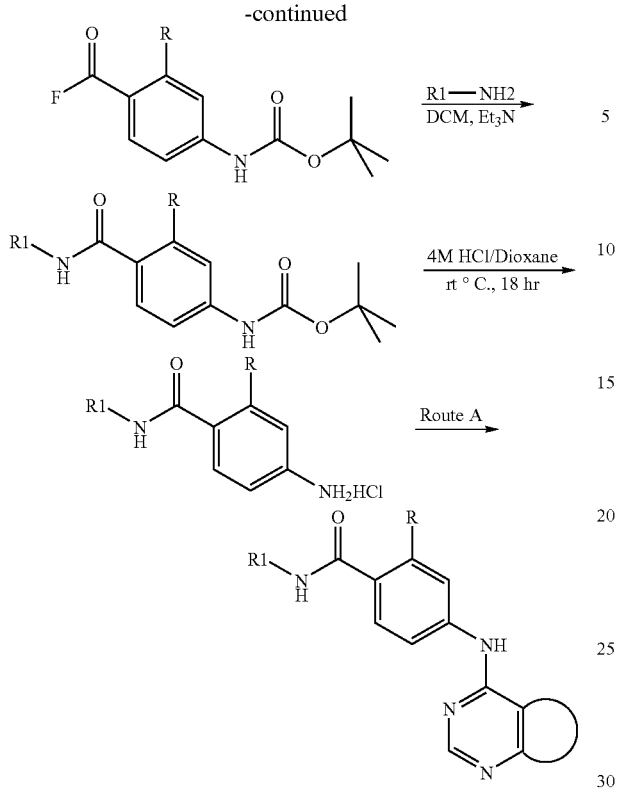

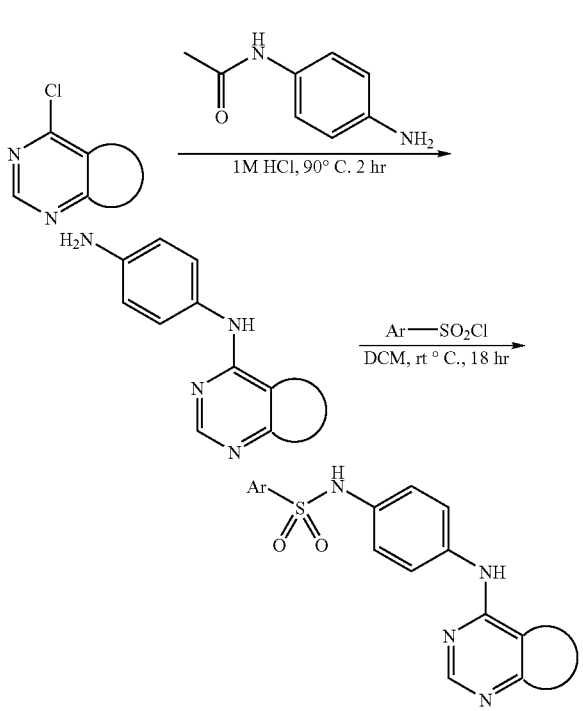

BOC Protection

The amino-benzoic acid (1.0 eq) was suspended in dioxane (20 vol) and a solution of NaOH (0.95 eq) in water (50 vol) added over 10 minutes. The mixture was then cooled to 0° C. and a solution of di-tert-butyl dicarbonate (1.4 eq) in dioxane added. The reaction mixture was then stirred at room temperature for 18 hours before quenching with citric acid (1.1 eq). The resultant precipitate was isolated by filtration, washed with water and dried to give the desired product.

Fluorination

The BOC protected amino-benzoic acid (1.0 eq) was suspended in DCM (10 vol) and the suspension cooled to −78° C. DAST (1.1 eq) was then added to the suspension drop-wise and the reaction left to stir at −78° C. Once the reaction was complete, the mixture was allowed to warm to room temperature and then poured into saturated NaHCO$_3$ (aq) solution. The mixture was then extracted with DCM twice, the organic layers combined, washed with 5% NaHCO$_3$ (aq) solution, dried over sodium sulphate and the solvent removed in vacuo to give the desired product.

Amide Formation

The acid fluoride (1.0 eq) and amine (1.1 eq) were dissolved in DCM (50 vol) and triethylamine (1.5 eq) added. The reaction was then stirred at room temperature for 18 hours, 1 M HCl was added to the reaction and the organic layer separated, washed with waters washed with brine, dried over sodium sulphate and the solvent removed in vacuo to give the desired product.

BOC Deprotection

The BOC protected aniline (1.0 eq) was suspended in 4 M HCl in dioxane (30 vol) and stirred at room temperature for 18 hours. The resultant precipitate was isolated by filtration and washed with diethyl ether. This gave the desired product as the HCl salt.

S$_N$Ar

As for route A.

Route X

S$_N$Ar

As for route A

Sulfonamide Formation

The pyrimidyl diamine (1.0 eq) was dissolved in DCM (20 vol), the sulfonyl chloride added and the reaction stirred at room temperature for 18 hours. The solvent was then removed in vacuo and the resultant residue purified using semi-preparative HPLC to give the desired compound.

The particularly preferred compound (compound 15)

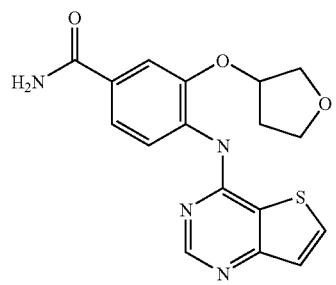

may be prepared as follows:

Synthetic Route

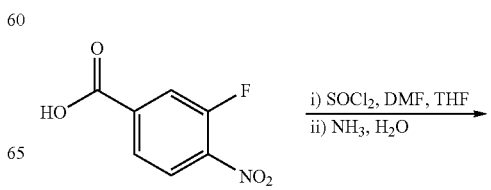

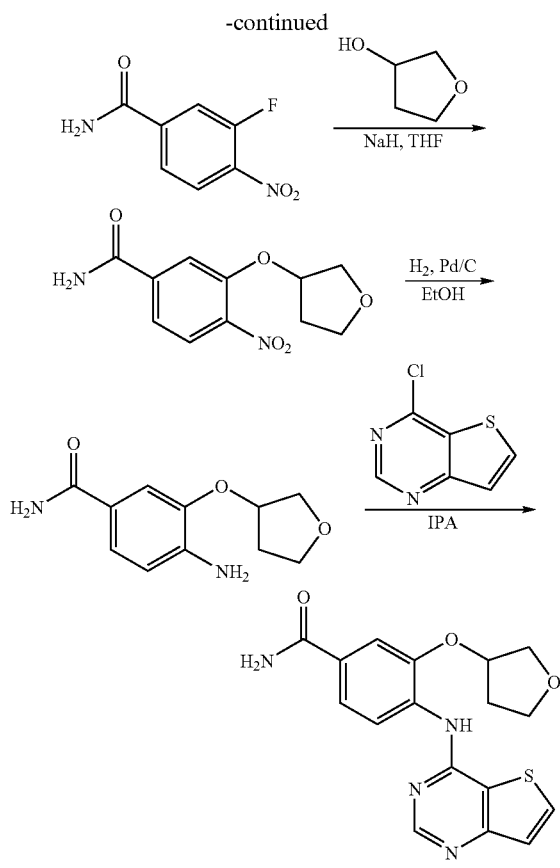

3-Fluoro-4-nitrobenzamide

To a solution of 3-fluoro-4-nitrobenzene carboxylic acid (18.0 g 1.0 eq, 0.10 mol) in THF (360 ml) at 0° C. was added thionyl chloride (56.7 ml, 8.0 eq, 0.78 mol) and DMF (1 ml.). The reaction was warmed to room temperature and stirred for 3.5 hours, after this point all starting material had been consumed. Thionyl chloride was then removed in vacuo to give 3-fluoro-4-nitrobenzoyl chloride as a yellow solid. This was dissolved in DCM (360 ml) and the solution added dropwise to a cooled solution of 880 ammonia in water (360 ml) with vigorous stirring. After the addition the reaction was stirred at room temperature for 15 minutes. The resultant precipitate was collected by filtration, and the filtrate was then filtered a further two more times. The three precipitates were each washed with cyclohexane (2×100 ml), dried in vacuo and combined to give the title compound as a yellow solid (13.32 g, 72 mmol, 74%). LCMS: [M+H]$^+$=na, Rt=1.41 min, 100% purity.

4-Nitro-3-(tetrahydrofuran-3-yloxy)-benzamide

To a solution of 3-hydroxytetrahydrofuran (2.57 ml, 1.2 eq, 23.0 mmol) in THF (50 ml) was added sodium hydride as a 60% dispersion in oil (0.84 g, 1.1 eq, 20.91 mmol) this mixture was then stirred at 0° C. for 30 minutes. The preceding mixture was added dropwise to a solution of 3-fluoro-4-nitrobenzamide (3.5 g, 1.0 eq, 19.01 mmol) in THF (30 ml) and stirred at room temperature for 3.5 hours. The reaction was quenched with water and extracted with DCM (3×50 ml), the organics were combined, dried over sodium sulphate, filtered and the solvent removed in vacuo to give the title compound as a yellow solid (4.77 g, 18.9 mmol, 96% corrected). LCMS: [M+H]$^+$=253, Rt=1.41 min, 100% purity

4-Amino-3-(tetrahydrofuran-3-yloxy)-benzamide

To a solution of 4-nitro-3-(tetrahydrofuran-3-yloxy)-benzamide (4.77 g, 18.15 mmol) in ethanol (200 ml) was added 10% palladium on carbon (0.5 g, 10% w/w) and the flask rinsed with an additional portion of ethanol (20 ml). The reaction was then purged with a nitrogen atmosphere, placed under a H$_2$ (g) atmosphere and stirred at room temperature for 18 hours. The reaction was then purged with N$_2$ (g) and filtered through a celite pad. The pad was washed with ethanol (100 ml) and the filtrate concentrated to dryness in vacuo to give the title compound as a white solid (4.22 g, 18.9 mmol, 100% corrected). LCMS: [M+H]$^+$=223, Rt=1.01 min, 100% purity

3-(Tetrahydrofuran-3-yl oxy)-4-(thieno[3,2-d]pyrimidin-4-yl amino)-benzamide The reaction was carried out in 4 batches using ACE pressure tubes. The 4-amino-3-(tetrahydrofuran-3-yloxy)-benzamide (0.52 g, 1.0 eq, 2.34 mmol) was added to a solution of 4-chlorothieno[3,2-d]pyrimidine (0.40 g, 1.0 eq, 2.34 mmol) in IPA (4 ml). The reaction mixtures were then stirred at 120° C. for 18 hours before being allowed to cool. 28% w/w Ammonium hydroxide solution (4 ml) followed by water (8 ml) were added and the reactions combined. The precipitate was isolated by filtration, washed with water (4×50 ml), dried on the sinter, washed with cyclohexane (8×50 ml), and then dried in vacuo to give the title compound as an off-white solid (2.71 g, 7.6 mmol, 81%). LCMS: [M+H]$^+$=357; Rt=1.27 min, 100% purity.

Example 2

Kinase Fluorescence Polarization Assays

Assay principle: Inhibitory potency of compounds against Mnk1, Mnk2a and other kinases was assessed with assays based on a format known to those skilled in the art as the indirect (competitive) fluorescence polarization. The assay detection system comprises a small fluorophore-labeled phospho-peptide (termed ligand) bound to a phospho-specific antibody. The product generated by the kinase reaction competes with the ligand for antibody binding. Based on the larger molecular volume of the bound ligand, which results in a lower rotation rate in solution, its emitted light has a higher degree of polarization than the one from the free ligand.

Description of the Specific Homogenous Kinase Assay

Example 2a

Mnk1 and Mnk2a In Vitro Kinase Assay

As a source of enzyme, human Mnk1 and human Mnk2a were expressed as GST fusion proteins in *E. coli*, purified to >80% homogeneity by glutathione affinity chromatography and activated in vitro with pre-activated ERK2. In brief, the open reading frames of human Mnk1 and Mnk2a were amplified from cDNA using the forward/reverse primer pairs

```
SEQ ID NO: 1    5'TTTAGGATCCGTATCTTCTCAAAAGTTGG/

SEQ ID NO: 2    5'CTGGGTCGACTCAGAGTGCTGTGGGCGG
```

-continued and

SEQ ID NO: 3    5'ACAG<u>GGATCC</u>GTGCAGAAGAAACCAGCC/

SEQ ID NO: 4    5'GAT<u>GGTCGAC</u>TCAGGCGTGGTCTCCCACC (utilized restriction sites underlined), respectively, and cloned into the BamHI and SalI sites of the vector pGEX-4T1 (Amersham, Sweden, cat. no. 27-4580-01). These constructs allow prokaryotic expression of Mnk1 or Mnk2a as fusion protein with a N-terminal glutathione. S-transferase (GST) tag, referred to as GST-Mnk1 or GST-Mnk2a. The following expression and purification procedure was identical for GST-Mnk1 and GST-Mnk2a, referring in general to GST-Mnk, when not distinguishing between the two isoforms. Expression of GST-Mnk was in *E. coli* BL21 (Merck Biosciences, Germany, cat. no. 69449). Cells were grown in LB-Bouillon (Merck, Germany, cat. no. 1.10285) supplemented with 100 µg/ml ampicillin (Sigma, Germany, cat. no. A9518) at 37° C. When the culture had reached a density corresponding to an $A_{600}$ of 0.8, an equal volume of ice cold LB/ampicillin was added, the culture transferred to 25° C. and induced for 4 h with 1 mM isopropyl thiogalactoside (IPTG, Roth, Germany, cat. no. 2316.4). Cells harvested by centrifugation were resuspended in 10 ml lysis buffer (50 mM tris(hydroxymethyl)aminomethane hydrochloride (Tris/HCl, Sigma, Germany, cat. no. T5941) pH 7.5, 300 mM sodium chloride (NaCl, Sigma, Germany, cat. no. S7653), 5% (w/v) glycerol (Sigma, Germany, cat. no. G5516), 3 mM DTT dithiotreitol (DTT, Sigma, Germany, cat. no. D9779)) per gram wet weight cell pellet. Lysates were prepared by disruption of cells with a sonifier and subsequent clearing by centrifugation at 38000 g for 45 min at 4° C.

The lysate was applied to a GSTPrep FF 16/10 column (Amersham, Sweden, cat. no. 17-5234-01) equilibrated with lysis buffer. Removal of unbound material was with 3 column volumes (CV) lysis buffer. Elution was with 2 CV of elution buffer (50 mM Tris/HCl pH 7.5, 300 mM NaCl, 5% (w/v) glycerol, 20 mM glutathione (Sigma, Germany, cat. no. G4251)). Peak fractions were pooled and the protein transferred into storage buffer (50 mM Tris/HCl pH 7.5, 200 mM NaCl, 0.1 mM ethylene glycol-bis(2-aminoethylether)-N,N,N',N'-tetraacetic acid (EGTA, Aldrich, Germany, cat. no. 23, 453-2), 1 mM DTT, 10% (w/v) glycerol, 0.5 M sucrose (Sigma, Germany, cat. no. S0389) by gel filtration on a PD10 desalting column (Amersham, Sweden, cat. no. 17-0851-01). Aliquots were shock frozen in liquid nitrogen and stored at −80° C.

Activation of Mnk1 and Mnk2a was at a concentration of 2.5 µM of either purified GST-Mnk1 or GST-Mnk2a by incubation with 150 nM pre-activated NHis-ERK2 (see ERK2 assay for preparation) and 50 µM adenosine triphosphate (ATP, Sigma, cat. no. A2699) in a buffer comprising 20 mM N-(2-hydroxyethyl)piperazine-N'-(2-ethanesulfonic acid) (HEPES, Fluka, Germany, cat. no 54459)/potassium hydroxide (KOH, Roth, Germany, cat. no 6751.1) pH 7.4, 10 mM magnesium chloride ($MgCl_2$, Sigma, Germany, cat. no. M2670), 0.25 mM DTT, 0.05% (w/v) polyoxyethylene 20 stearylether (Brij 78, Sigma, Germany, cat. no. P4019) (HMDB buffer) for 45 min at 30° C. After the incubation, the preparation was aliquoted into single-use samples, shock frozen in liquid nitrogen, stored at −80° C. and utilized for Mnk1 or Mnk2a kinase assays as detailed below. The presence of activating kinase has been tested to not interfere with the Mnk activity assay.

SUBSTRATE: A carboxy-terminal amidated 12mer peptide with the sequence

SEQ ID NO: 5    TATKSG<u>S</u>TTKNR, derived from the amino acid sequence around serine 209 of the eukaryotic translation initiation factor 4E (eIF4E) has been synthesized and purified by high performance liquid chromatography (HPLC) to >95% (Thermo, Germany). The serine residue phosphorylated by Mnk kinases is underlined.

LIGAND: The peptide TATKSG-pS-TTKNR, containing an amidated carboxy-terminus and conjugated at the amino-terminus with the oxazine derived fluorophore depicted below was synthesized and used as ligand.

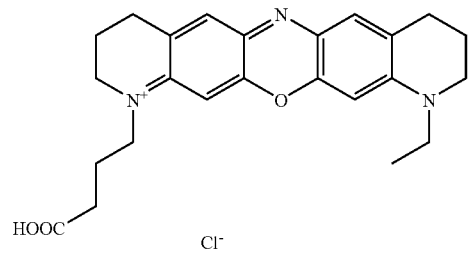 [SMILES: CCN1CCCc2cc3c(cc21)Oc1cc2c(cc1=N3)CCC[N+]=2CCCC(=O)O ; [Cl-]]

ANTIBODY: SPF New Zealand White Rabbits have been immunized according to standard protocols with the peptide NH2-CTATKSG-pS-TTKNR-CONH2, coupled to keyhole limpet hemocyanin (KLH). The immune globulin G (IgG) fraction was purified from serum of boosted animals by techniques known in the art. In brief, serum was subjected to protein A affinity chromatography. Eluted material was precipitated at 50% cold saturated ammonium sulfate, pellets dissolved and desalted. The resulting material was appropriate for use in below described assay without further antigen-specific purification.

ASSAY SETUP: Inhibition of kinase activity of Mnk1 and Mnk2a was assessed with the same assay system, using pre-activated GST-Mnk1 or GST-Mnk2a, respectively. The kinase reaction contains 30 µM substrate peptide, 20 µM ATP, 60 nM ligand and one of either 25 nM pre-activated Mnk1 or 2.5 nM pre-activated Mnk2a. The reaction buffer conditions are 16 mM HEPES/KOH pH 7.4, 8 mM $MgCl_2$, 0.4 mM DTT, 0.08% (w/v) bovine serum albumin (BSA, Sigma, Germany, cat. no. A3059), 0.008% (w/v) Pluronic F127 (Sigma, Germany, cat. no. P2443), 3% (v/v) DMSO (Applichem, Germany, cat. no. A3006). The kinase reaction is at 30° C. for 40 min. The kinase reaction is terminated by addition of 0.67 reaction volumes of 1 µM antibody in 20 mM HEPES/KOH pH 7.4, 50 mM ethylenediaminetetraacetic acid, disodium salt (EDTA, Sigma, Germany, cat. no. E5134), 0.5 mM DTT, 0.05% (w/v) polyoxyethylene-sorbitan monolaureate (Tween 20, Sigma, Germany, cat. no. P7949). After 1 h equilibration time at room temperature, samples are subjected to fluorescence polarization measurement. The fluorescence polarization readout was generated on an Analyst AD multimode reader (Molecular Devices, Sunnyvale, Calif., USA) equipped with a DLRP650 dichroic mirror (Omega Opticals, Brattleboro, Vt., USA, cat. no. XF2035), a 630AF50 band pass filter (Omega Opticals, Brattleboro, Vt., USA, cat. no. XF1069) on the excitation and a 695AF55 band pass filter on the emission side (Omega Opticals, Brattleboro, Vt., USA, cat. no. XF3076).

Example 2b

ERK2 In Vitro Kinase Assay

KINASE: As a source of enzyme, human ERK2 was expressed as N-terminal hexa-histidin fusion protein in *E. coli*, purified to >80% homogeneity by immobilized metal ion affinity chromatography (IMAC) and activated in vitro with a constitutively active mutant of MEK1.

In brief, the open reading frame of human ERK2 was amplified from cDNA using the forward/reverse primer pair SEQ ID NO: 6    5'AGCC<u>GTCGAC</u>GCGGCGGCGGCGGCGGCGGGC/

SEQ ID NO: 7    G'TGAC<u>AAGCTT</u>AAGATCTGTATCCTGGCTGG (utilized restriction sites underlined) and cloned into the SalI and HindIII sites of the vector pQE81L (Qiagen, Germany, cat, no. 32923). This construct allows prokaryotic expression of ERK2 as fusion protein with a N-terminal hexa-histidin tag, referred to as NHis-ERK2. Expression of NHis-ERK2 was in *E. coli* BL21. Cells were grown in LB-Bouillon supplemented with 100 μg/ml ampicillin at 37° C. When the culture had reached a density corresponding to an $A_{600}$ of 0.8, an equal volume of ice cold LB/ampicillin was added, the culture transferred to 25° C. and induced for 4 h with 1 mM IPTG. Cells harvested by centrifugation were resuspended in 10 ml lysis buffer (50 mM Tris/HCl pH 7.5, 300 mM NaCl, 5% (w/v) glycerol, 10 mM β-mercapto ethanol (Sigma, Germany, cat. no. M3148) per gram wet weight cell pellet. Lysates were prepared by disruption of cells with a sonifier and subsequent clearing by centrifugation at 38000 g for 45 min at 4° C.

The lysate was applied to a column containing 25 ml Ni-NTA Superflow matrix (Qiagen, Germany, cat. no. 1018611) equilibrated with lysis buffer. Removal of unbound material was with 3 column volumes (CV) wash buffer (50 mM Tris/HCl pH 7.5, 300 mM NaCl, 5% (w/v) glycerol, 10 mM β-mercapto ethanol, 20 mM imidazol (Sigma, Germany, cat. no. 12399)/HCl pH 7.5). Elution was with 2 CV of elution buffer (50 mM Tris/HCl pH 7.5, 300 mM NaCl, 5% (w/v) glycerol, 300 mM imidazol). Peak fractions were pooled and the protein transferred into storage buffer (50 mM Tris/HCl pH 7.5, 200 mM NaCl, 0.1 mM EGTA, 1 mM DTT, 10% (w/v) glycerol, 0.5 M sucrose) by gel filtration on a PD10 desalting column. Aliquots were shock frozen in liquid nitrogen and stored at −80° C.

The open reading frame of human MEK1 was amplified from cDNA using the forward/reverse primer pair SEQ ID NO: 8    5'GTCC<u>GGATCC</u>CCCAAGAAGAAGCCGACGCCC SEQ ID NO: 9    5'  TCCC<u>GTCGAC</u>TTAGACGCCAGCAGCATGGG (utilized restriction sites underlined) and cloned into the BamHI and SalI sites of the vector pQE80L (Qiagen, Germany, cat. no. 32923). By techniques known in the art, the serine codons 212 and 214 were mutagenized to encode aspartate and glutamate. The resulting expression construct is referred to as NHis-MEK1 SSDE. This construct allows prokaryotic expression of MEK1 as a constitutively active mutant. NHis-MEK1 SSDE was expressed and purified under the conditions described for NHis-ERK2.

Activation of NHis-ERK2 was at a concentration of 11.3 μM of purified enzyme by incubation with 1 μM NHis-MEK1 SSDE and 100 μM ATP in a buffer comprising 20 mM HEPES/KOH pH 7.4, 10 mM $MgCl_2$, 0.25 mM DTT, 0.05% (w/v) Brij 78 (HMDB buffer) for 20 min at 30° C. After the incubation, the preparation was aliquoted into single-use samples, shock frozen in liquid nitrogen, stored at −80° C. and utilized for ERK2 kinase assay as detailed below and for activation of Mnk1 and Mnk2a as described above. The presence of MEK1 SSDE has been tested to not interfere with the ERK2 activity assay.

SUBSTRATE: A carboxy-terminal amidated 17mer peptide with the sequence

SEQ ID NO: 10    FFKNIVTPR<u>T</u>PPPSQGK (synthesis by Thermo, Germany), derived from the amino acid sequence around threonine 98 of the myelin basic protein (MBP) has been synthesized and purified by HPLC to >95%. The relevant residue phosphorylated by ERK2 is underlined.

LIGAND: The peptide KNIVTPR-pT-PPPS, containing an amidated carboxy-terminus and conjugated at the amino-terminus with the fluorophore 5-carboxytetramethyl-rhodamine (5-TAMRA) was purchased from Thermo (Germany) and used as ligand.

ANTIBODY: Anti-phospho-MBP antibody (clone P12) was purchased from Upstate, Waltham, Mass., USA (cat. no. 05-429).

ASSAY SETUP: The kinase reaction contains 60 μM substrate peptide, 10 μM ATP and 30 nM pre-activated NHis-ERK2. The reaction buffer conditions are 16 mM HEPES/KOH pH 7.4, 8 mM $MgCl_2$, 0.4 mM DTT, 0.08% (w/v) BSA, 0.008% (w/v) Pluronic F127, 3% (v/v) DMSO.

The kinase reaction is at 30° C. for 40 min. The kinase reaction is terminated by addition of 0.67 reaction volumes of 5 nM ligand and 50 nM antibody in 20 mM HEPES/KOH pH 7.4, 50 mM EDTA, 0.5 mM DTT, 0.05% (w/v) Tween 20. After 30 min equilibration time at room temperature, samples are subjected to fluorescence polarization measurement. The fluorescence polarization readout was generated on an Analyst AD multimode reader (Molecular Devices, Sunnyvale, Calif., USA) equipped with a 561 nm dichroic mirror (Molecular Devices, Sunnyvale, Calif., USA, cat. no. 42-000-0048), a 550/10 nm band pass filter (Molecular Devices, Sunnyvale, Calif., USA, cat. no. 42-000-0130) on the excitation and a 580/10 nm band pass filter (Molecular Devices, Sunnyvale, Calif., USA, cat. no. 42-000-0034) on the emission side.

It has been shown that the particular preferred compound of the invention exhibit $IC_{50}$ values below 10 micromolar in in vitro biological screening assays for inhibition of Mnk 1 and/or Mnk 2 kinase activity.

Without being exhaustive, the following principles and methods may be employed to identify and select therapeutic compounds for use in treating inflammatory diseases and conditions as contemplated by the present invention as defined above and in the claims.

As a general principle, a system which has not been exposed to an inflammatory stimulus is exposed to such stimulus and the candidate therapeutic compound. Such system may comprise cultured cells, or components of cells, or isolated organs or tissues from animals. Alternatively, animals can be exposed to an inflammatory stimulus and the compound.

Specifically, a control group is given a known amount of inflammatory stimulus. Treatment groups are exposed to the same amount of inflammatory stimulus as well as aliquots of the candidate therapeutic compound. Inflammatory response in each group are detected by conventional means known to those of skill in the art and compared.

In particular, the following assays may be used:

Assay Utilizing Peripheral Blood Mononuclear Cells (e.g. Newton, J Leukoc Biol 39:299-311, 1986)

Human peripheral blood mononuclear cells are prepared from the peripheral blood using a ficoll-hypaque density separation (Hansell et al., J Imm Methods 145:105, 1991). Cells are cultured in appropriate medium and at appropriate density. Such density could be $10^5$ to $10^6$ cells per well of a 96-well plate. An appropriate culture medium could comprise RPMI 1640 supplemented with 10% fetal calf serum. Cells are incubated with serial dilutions of test compounds for a given time. This incubation is followed by an inflammatory stimulus applied to the cells. This stimulus could comprise LPS, or another agent, or a combination of agents. After yet another incubation, supernatant is withdrawn from the compound treated and control cells and analyzed for molecules useful for monitoring the inflammatory response. This analysis may comprise detection and quantification of cytokines (e.g., interleukins, interferones, tumor necrosis factors, chemokines), or leukotrines, or prostaglandins, or their derivatives. Detection may be with, e.g. commercially available enzyme-linked immunosorbent assays (ELISAs).

Assay for Inhibition of Cytokine Production in Lipopolysaccharide Stimulated Mice or Rats Injection of lipopolysaccharide (LPS) into mice or rats induces a rapid release of soluble cytokines into the periphery (e.g. Wichterman et al., J Surg Res 9:189-201, 1980, Beutler 1992. Tumor necrosis factors: the molecules and their emerging role in medicine. Raven Press, New York, N.Y.).

Prior to LPS injection, compounds of the invention are given either orally, or s.c., or i.v. Compounds may be given acute or sub acute. After a given time or at several given time points after LPS injection, blood is withdrawn from animals and is analysed for cytokine levels. Effects in compound treated and sham treated animals are compared.

Assay for Inhibition of Adjuvant Arthritis (Pearson, Proc Soc Exp Biol Med 91:95-101, 1956)

Adjuvant arthritis is an acute inflammatory disease induced in certain rat strains by the administration of heat-killed mycobacteria dispersed in incomplete Freund's adjuvant. The disease is manifest by severe joint swelling, mainly of the ankles and feet.

Treatment groups and control groups of rats, e.g. Lewis rats, are immunized with heat-killed *mycobacteria tuberculosis* emulsified in incomplete Freund's adjuvant. Thereafter, the control groups receive mock treatment, while the treatment groups receive compounds of the invention. Administration may be either orally, or s.c., or i.v. Treatment may be acute or sub acute. During the treatment phase the arthritis progression is determined by scoring the swelling of limbs.

The following animal models may be utilized as described above by the general testing principle to identify and select compounds for the indicated inflammatory diseases and conditions.

Animal Models of Inflammatory and Rheumatoid Arthritis

Animal models reflecting disease progression of inflammatory and rheumatoid arthritis have been reviewed by Brand (Comp Med 55(2):114-122, 2005). Specifically models of antigen-induced arthritis (Dumonde and Glynn, Br J Exp Pathol 43:373-383, 1962), adjuvant arthritis (Pearson, Proc Soc Exp Biol Med 91:95-101, 1956), antibody arthritis (Terato et al., J Immunol 148:2103-2108, 1992) or collagen-induced arthritis (Trentham et al., J Exp Med 146:857-868, 1977; Courtenay et al., Nature 283:666-668, 1980) may be employed to select specific compounds of the invention.

Animal Models of Inflammatory Bowel Diseases and Related Disorders

Animal models of inflammatory bowel diseases such as Crohn's disease and ulcerative colitis have been reviewed by Wirtz and Neurath (Int J Colorectal Dis 15(3):144-60, 2000). States reflecting the pathogenesis of chronic intestinal inflammation may be induced by administration of formaldehyde in combination with immune complexes (Hodgson et al., Gut 19:225-232, 1978; Mee et al., Gut 20:1-5, 1979), acetic acid (MacPherson and Pfeiffer, Digestion 17:135-150, 1978), indomethacin (Banerjee and Peters, Gut 31:1358-1364, 1990; Yamada et al., Inflammation 17:641-662, 1993), dextran sulfate sodium(Okayasu et al., Gastroenterology 98:694-702, 1990), or haptens like trinitrobenzene sulfonic acid (TNBS)/dinitrobenzene sulfonic acid (DNBS) (Morris et al., Gastroenterology 96:795-803, 1989;

Elson et al., J Immunol 157:2174-2185, 1996; Neurath et al., J Exp Med 182:1281-1290, 1995; Yamada et al., Gastroenterology 102:1524-1534, 1992; Dohi et al., J Exp Med 189:1169-1180, 1999) or oxazolone (Ekstrom, Scand J Gastroenterol 33:174-179, 1998; Boirivant et al., J Exp Med 188:1929-1939, 1998).

Animal Models of Septic Shock

Animal models of septic shock expose specimen to lipopolysaccharide (LPS), gram-negative or gram-positive bacteria, or combinations thereof (Wichterman al., J Surg Res 29:189-201, 1980; Fink and Heard, J Surg Res 49(2):186-96, 1990). The rodent model of cecal ligation and puncture (CLP) resembles the situation of bowel perforation and mixed bacterial infection of intestinal origin (Baker et al., Surgery 94:331-335, 1983).

Animal Model of Psoriasis

To invest the suitability of compounds for the treatment of psoriasis, the human psoriatic skin xenotransplantation model (Nickoloff, Arch Dermatol 135:1104-1110, 1999; Nickoloff, J Invest Dermatol Symp Proc 5:67-73, 2000) may be utilized.

Animal Model of Allergic Asthma

In a commonly employed rodent model of allergic asthma animals are sensitized to an antigen (e.g. ovalbumin) and are subsequently challenged with the same antigen by inhalation of an aerosol (e.g. Fujitani et al., Am J Respir Crit. Care Med 155:1890-1894, 1997; Kanehiro et al., Am J Respir Crit Care Med 163:173-184, 2001; Henderson et al., Am J Respir Crit Care Med 165:108-116, 2002; Oh et al., J Immunol 168:1992-2000, 2002).

The in vivo pharmacological activity of compound 15 has been determined in mice.

Material and Methods

Animals

BKS.Cg-m+/+Lepr$^{db}$/J (Charles River Laboratories) male mice (commonly referred to as db/db mice) are deficient in the adipokine Leptin due a spontaneous point mutation. They are maintained on the C57BL6/J strain.

Mice are housed four by cage at a temperature of 22-24° C. and a day/night cycle of dg7014/10 hours (05:00-19:00-05:00), and obtain standard chow and tap water ad libitum. Mice are allowed to adapt to housing and environment for 14 days prior to substance administration.

Substance Administration

Compound suspensions in 0.3% Methylcellulose in saline are prepared freshly just prior to administration.

Substances will be administered by oral gavage in the morning at 07:00, one hour before determining fed blood glucose levels and body weight. In the evening, substance is administered between 17:00 and 18:00. Animals are visually monitored for 1 hour after the administrations.

Dosing

Dosing is chosen based on the results of pharmacokinetic (PK) and dose tolerability studies.

Control Substances

Rosiglitazone (Avandia®) belongs to the thiazolidinedione class of PPARgamma agonist drugs, which exert their main therapeutic effects by improving insulin sensitivity in type 2 diabetes with marked effects on glucose homeostasis and glucose tolerance.

Study Schedule

Animals are being supplied one week in advance to allow for adaptation to housing and environment. During that time, body weight and fed blood glucose are measured daily.

The premonitoring phase (body weight, blood glucose, food, water, ITT, oGTT) starts at day-1-2. Test and control substance administration begins at day 0. During the study, the recording of body weight and fed blood glucose is continued one hour after compound administration in the morning. Oral glucose tolerance tests as well as insulin tolerance tests are performed. The study ends at day 14, where the animals are sacrificed and organs, tissues, and fluids are sampled for further analysis.

Readouts

Bodyweight and bloodglucose were measured three times a week. At the end of the study pancreatic insulin content and plasma parameters were determined.

Oral Glucose Tolerance Test

Over night fasted animals (14 h fasted), receive an oral glucose bolus (2 g glucose/kg body weight) 2 h after the morning application. Shortly before (t=0 min) and at the following time points blood glucose values are measured by the tail tip method: 15, 30, 60, 90, 120 and 180 min.

Insulin Tolerance Test

Fully fed mice receive a human Insulin i.p. injection (Lilly; 0,75 U/kg; dilution with 0,9% NaCl) 2 hours after the morning application. Food is withdrawn after Insulin gift. Shortly before (t=0 min) and at the following time points blood glucose values are measured by the tail tip method: 15, 30, 45, 75 and 135 min.

Results

During the study the bodyweight was measured three times a week. The PPARgamma agonist Rosiglitazone was used as a control. Rosiglitazone treatment resulted in a significant increased in body weight compared to vehicle from d1 to d14

In contrast Mnk inhibitors show no difference to the vehicle treated animals, Mnk inhibitors are bodyweight neutral (FIG. 1).

FIG. 2 shows the random fed blood glucose during the study. There is a progressive improvement in blood glucose with the Mnk inhibitor compound 15.

Insulin tolerance test were performed at the end if the study. Treatment with Mnk inhibitors resulted in an improved insulin tolerance test, demonstrating an increased insulin sensitivity (FIG. 3).

Plasma analysis at the end of the study shows a clear reduction in circulating triglycerides by Mnk inhibitor treatment. In addition there was a significant reduction of NEFAs (FIG. 4).

Treatment with Mnk inhibitors also resulted in reduced plasma insulin and elevated pancreatic insulin content (FIG. 5). This is consistent with the observed improved insulin sensitivity.

The invention claimed is:

1. A compound of the formula (1)

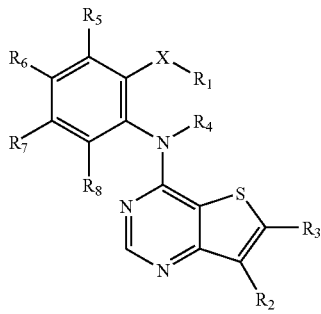

wherein X is O;
$R_1$ is $C_{3-6}$alkyl optionally substituted with one or more halogen atoms, $C_{3-10}$ cycloalkyl, or 3 to 10 membered heterocycloalkyl comprising a heteroatom selected from N and O and, optionally substituted with one or more $R_9$;
$R_2$ and $R_3$ are the same or different and are independently selected from hydrogen and $C_{1-6}$ alkyl;
$R_4$ is hydrogen, $C_{1-4}$ alkyl, urea, thiourea or acetyl optionally substituted with one or more $R_9$;
$R_5$, $R_7$ and $R_8$ are hydrogen;
$R_6$ is selected from, halogen, —C(O)N($R_{11}R_{11a}$) and —COO$R_{11}$;
$R_9$ is independently halogen; CN; COO$R_{11}$; O$R_{11}$; C(O)N($R_{11}R_{11a}$); S(O)$_2$N($R_{11}R_{11a}$); S(O)N($R_{11}R_{11a}$); S(O)$_2$$R_{11}$; N($R_{11}$)S(O)$_2$N($R_{11a}R_{11b}$); S$R_{11}$; N($R_{11}R_{11a}$); OC(O)$R_{11}$; N($R_{11}$)C(O)$R_{11a}$; N($R_{11}$)S(O)$R_{11a}$; N($R_{11}$)S(O)$R_{11a}$; N($R_{11}$)C(O)N($R_{11a}R_{11b}$); N($R_{11}$)C(O)O$R_{11a}$; OC(O)N($R_{11}R_{11a}$); oxo (=O); C(O)$R_{11}$; $C_{11b}$ alkyl; phenyl; $C_{3-7}$ cycloalkyl; or 5 or 6 membered saturated, unsaturated or aromatic heterocyclyl comprising at least one heteroatom selected from N, S and O; wherein $C_{1-6}$ alkyl, phenyl, $C_{3-7}$ cycloalkyl, and heterocyclyl are optionally substituted with one or more $R_{10}$;
$R_{10}$ is independently halogen; CN; O$R_{11}$; S(O)$_2$N($R_{11}R_{11a}$); S(O)N($R_{11}R_{11a}$); S(O)$_2$$R_{11}$; N($R_{11}$)S(O)$_2$N($R_{11a}R_{11b}$); S$R_{11}$; N($R_{11}R_{11a}$); OC(O)$R_{11}$; N($R_{11}$)C(O)$R_{11a}$; N($R_{11}$)S(O)$_2$$R_{11a}$; N($R_{11}$)S(O)$R_{11a}$; N($R_{11}$)C(O) N($R_{11a}R_{11b}$); N($R_{11}$)C(O)O$R_{11a}$; OC(O)N($R_{11}R_{11a}$); oxo (=O); C(O)$R_{11}$; $C_{1-6}$ alkyl; phenyl; $C_{3-7}$ cycloalkyl; or heterocyclyl;
$R_{11}$, $R_{11a}$, $R_{11b}$ are independently selected from the group consisting of hydrogen, $C_{1-6}$ alkyl, $C_{1-6}$ alkyl $C_{3-10}$ cycloalkyl, $C_{3-10}$ cycloalkyl, $C_{1-6}$ alkyl 3 to 10 membered heterocycloalkyl comprising at least one heteroatom selected from N, S and O, 3 to 10 membered heterocycloalkyl comprising at least one heteroatom selected from N, S and O, $C_{6-10}$ aryl, 5 to 10 membered heteroaryl comprising at least one heteroatom selected from N, S and O;
or a pharmaceutically acceptable salt thereof.

2. The compound according to claim 1, wherein $R_2$ and $R_3$ are hydrogen.

3. The compound according to claim 1, wherein $R_4$ is hydrogen.

4. The compound according to claim 1, wherein $R_6$ is selected from fluorine, COOH and C(O)NH$_2$.

5. A pharmaceutical composition comprising a compound according to claim 1 and a pharmaceutically acceptable carrier.

6. The pharmaceutical composition according to claim 5 further comprising an additional therapeutic agent.

7. The pharmaceutical composition according to claim 6 wherein the additional therapeutic agent is selected from an antidiabetic agent, a lipid lowering agent, a cardiovascular agent, an antihypertensive agent, a diuretic agent, a thrombocyte aggregation inhibitor, an antineoplastic agent or an anti-obesity agent.

8. The pharmaceutical composition according to claim 6, wherein the additional therapeutic agent is selected from human NPH insulin, human lente or ultralente insulin, insulin Lispro, insulin Aspatart, or insulin Glargine, atenolol, bisoprolol, metoprolol, esmolol, celiprolol, talinolol, oxprenolol, pindolol, propanolol, bupropanolol, penbutolol, mepindolol, sotalol, certeolol, nadolol, carvedilol, nifedipin, nitrendipin, amlodipin, nicardipin, nisoldipin, diltiazem, enalapril, verapamil, gallopamil, quinapril, captopril, lisinopril, benazepril, ramipril, peridopril, fosinopril, trandolapril, irbesatan, losartan, valsartan, telmisartan, eprosartan, olmesartan, hydrochlorothiazide, piretanid, chlorotalidone, mefruside, furosemide, bendroflumethiazid, triamterene, dehydralazine, acetylsalicylic acid, tirofiban-HCl, dipyramidol, triclopidin, iloprost-trometanol, eptifibatide, clopidogrel, piratecam, abciximab, trapidil, simvastatine, bezafibrate, fenofibrate, gemfibrozil, etofyllin, clofibrate, etofibrate, fluvastatine, lovastatine, pravastatin, colestyramide, colestipol-HCl, xantinol nicotinat, inositol nicotinate, acipimox, nebivolol, glycerolnitrate, isosorbide mononitrate, isosorbide dinitrate, pentaerythrityl tetranitrate, indapamide, cilazepril, urapidil, eprosartan, nilvadipin, metoprolol, doxazosin, molsidormin, moxaverin, acebutolol, prazosine, trapidil, clonidine, vinblastin, vincristin, vindesin, vinorelbin, podophylloxine derivatives, etoposid, teniposid, alkylating agents, nitroso ureas, cycloplonphamid, estamustin, melphalan, ifosfamid, mitoxantron, idarubicin, doxorubicin, bleomycin, mitomycin, dactinomycin, daptomycin, cytarabin, fluorouracil, fluoroarabin, gemcitabin, tioguanin, capecitabin, adriamydin/daunorubicin, cytosine arabinosid/cytarabine, 4-HC, and other phosphamides.

9. The pharmaceutical composition according to claim 5, wherein the pharmaceutically acceptable carrier is adapted for oral, parenteral, local, or topical administration.

10. The compound according to claim 1 selected from:

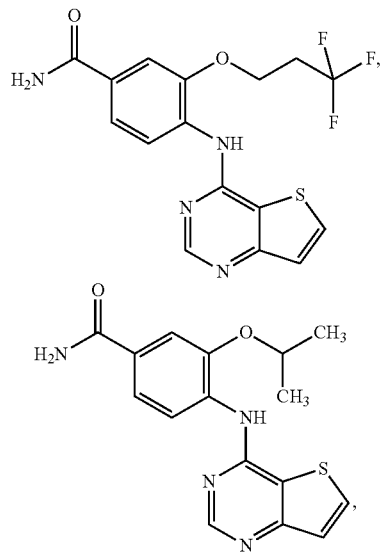

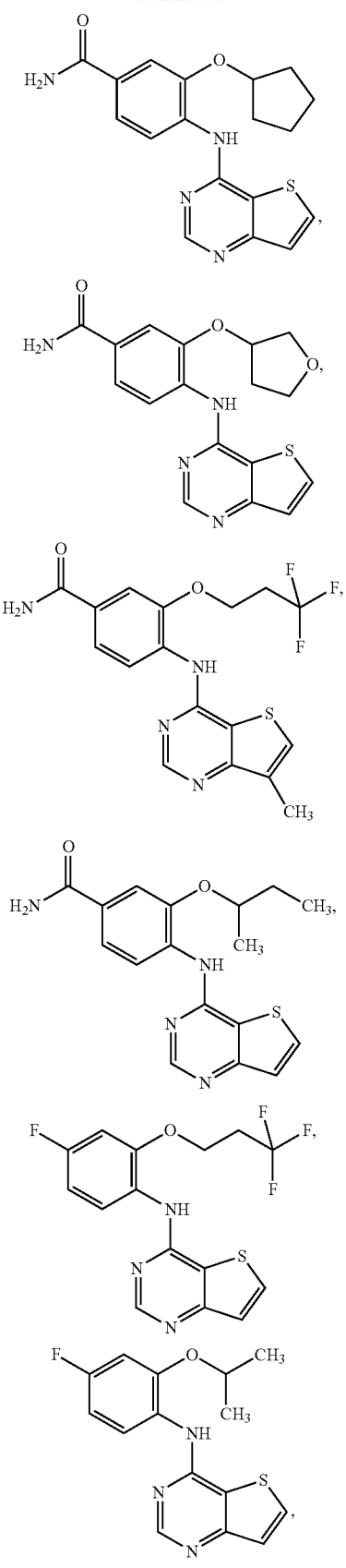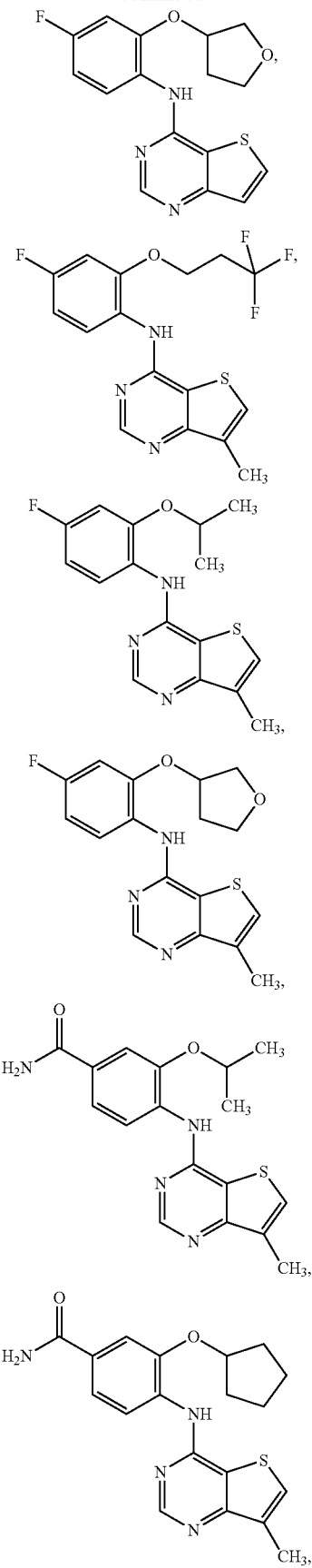

-continued
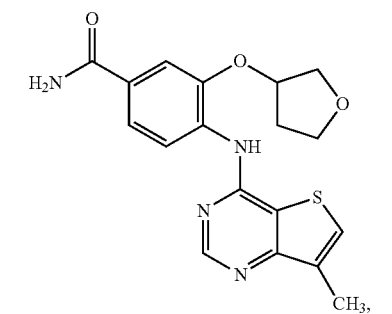
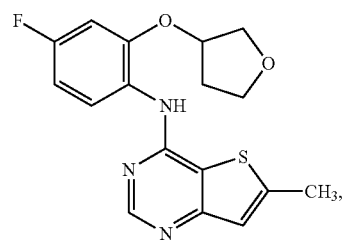
and
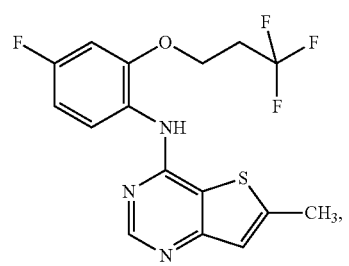
11. The compound according to claim 1 selected from the group consisting of
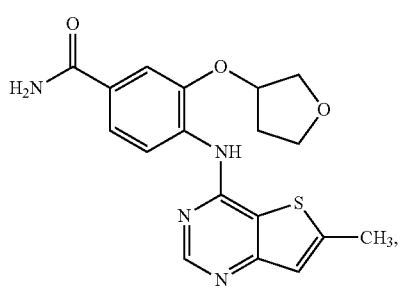
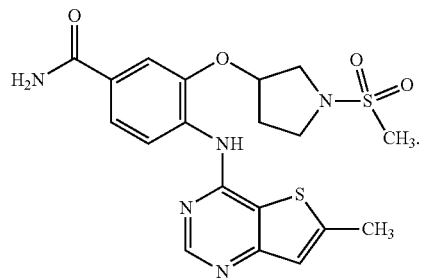 [SMILES: Cc1cc2ncnc(Nc3ccc(C(N)=O)cc3OC3CCN(S(C)(=O)=O)C3)c2s1]
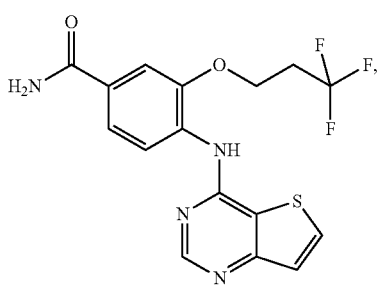

-continued
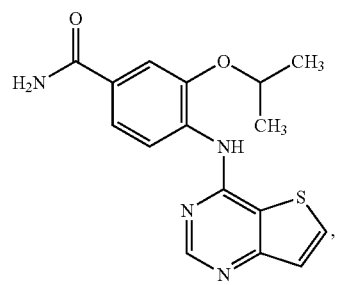
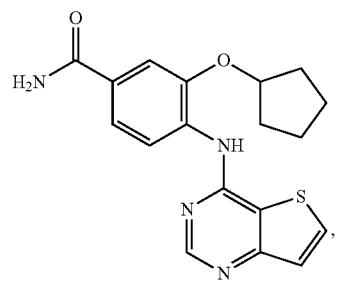 [SMILES: NC(=O)c1ccc(Nc2ncnc3ccsc23)c(OC2CCOC2)c1]
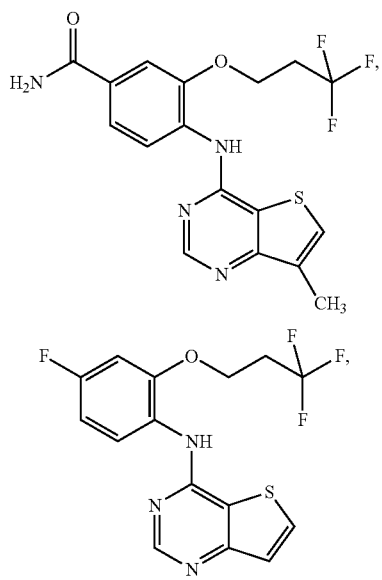
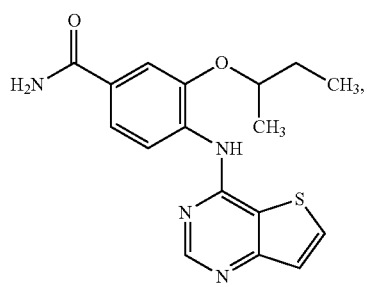
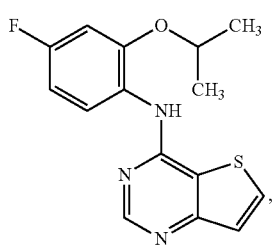
-continued
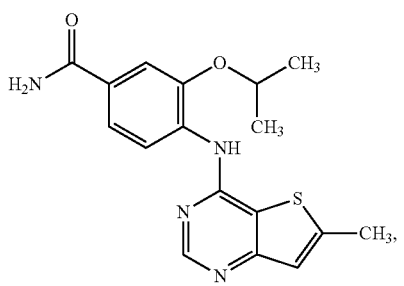
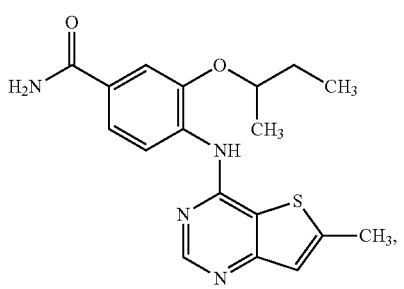
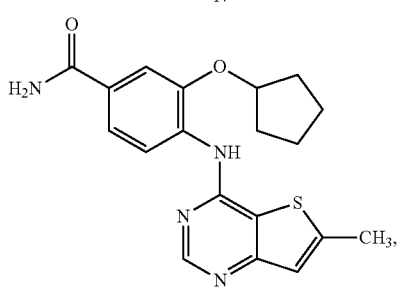
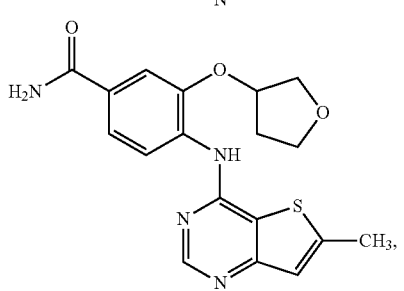
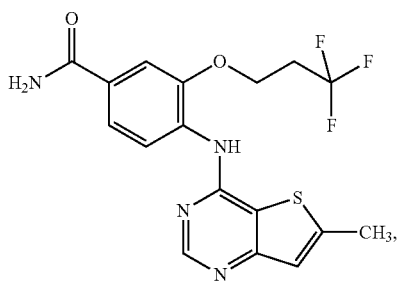
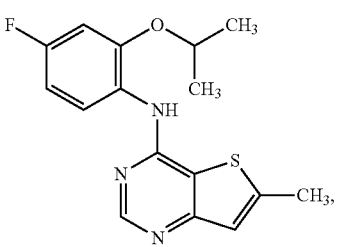

-continued
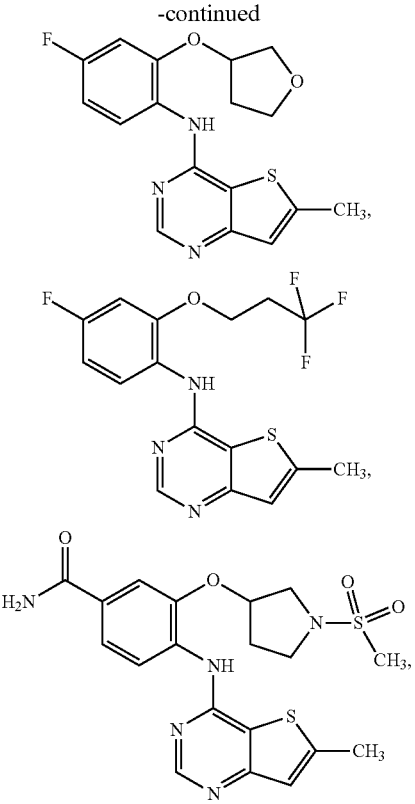
-continued
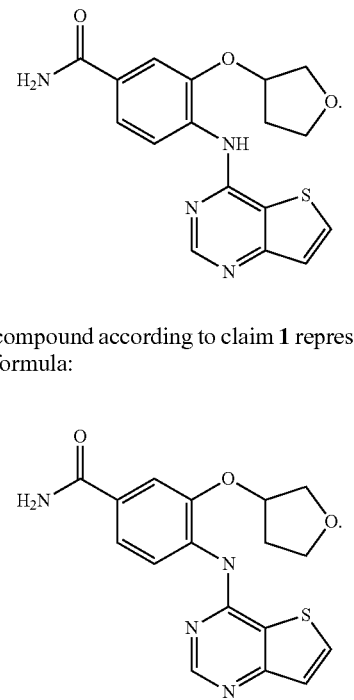
12. The compound according to claim 1 represented by the following formula:
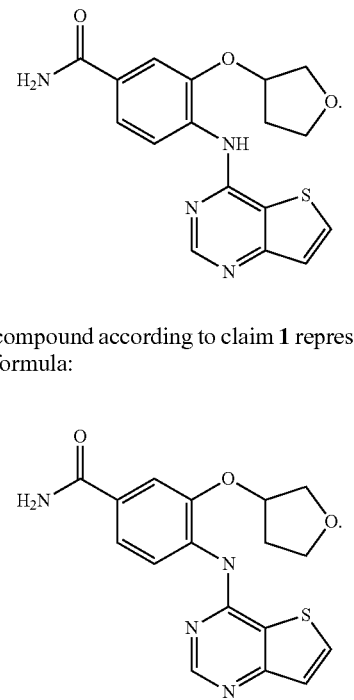
* * * * *

SEQUENCE LISTING

```
<160> NUMBER OF SEQ ID NOS: 10

<210> SEQ ID NO 1
<211> LENGTH: 29
<212> TYPE: DNA
<213> ORGANISM: Homo sapiens

<400> SEQUENCE: 1
tttaggatcc gtatcttctc aaaagttgg                                      29

<210> SEQ ID NO 2
<211> LENGTH: 28
<212> TYPE: DNA
<213> ORGANISM: Homo sapiens

<400> SEQUENCE: 2
ctgggtcgac tcagagtgct gtgggcgg                                       28

<210> SEQ ID NO 3
<211> LENGTH: 28
<212> TYPE: DNA
<213> ORGANISM: Homo sapiens

<400> SEQUENCE: 3
acagggatcc gtgcagaaga aaccagcc                                       28

<210> SEQ ID NO 4
<211> LENGTH: 29
<212> TYPE: DNA
<213> ORGANISM: Homo sapiens
```

-continued

```
<400> SEQUENCE: 4
gatggtcgac tcaggcgtgg tctcccacc                                    29

<210> SEQ ID NO 5
<211> LENGTH: 12
<212> TYPE: PRT
<213> ORGANISM: Homo sapiens

<400> SEQUENCE: 5

Thr Ala Thr Lys Ser Gly Ser Thr Thr Lys Asn Arg
1               5                   10

<210> SEQ ID NO 6
<211> LENGTH: 31
<212> TYPE: DNA
<213> ORGANISM: Homo sapiens

<400> SEQUENCE: 6
agccgtcgac gcggcggcgg cggcggcggg c                                 31

<210> SEQ ID NO 7
<211> LENGTH: 30
<212> TYPE: DNA
<213> ORGANISM: Homo sapiens

<400> SEQUENCE: 7
tgacaagctt aagatctgta tcctggctgg                                   30

<210> SEQ ID NO 8
<211> LENGTH: 31
<212> TYPE: DNA
<213> ORGANISM: Homo sapiens

<400> SEQUENCE: 8
gtccggatcc cccaagaaga agccgacgcc c                                 31

<210> SEQ ID NO 9
<211> LENGTH: 30
<212> TYPE: DNA
<213> ORGANISM: Homo sapiens

<400> SEQUENCE: 9
tcccgtcgac ttagacgcca gcagcatggg                                   30

<210> SEQ ID NO 10
<211> LENGTH: 17
<212> TYPE: PRT
<213> ORGANISM: Homo sapiens

<400> SEQUENCE: 10

Phe Phe Lys Asn Ile Val Thr Pro Arg Thr Pro Pro Ser Gln Gly
1               5                   10                  15

Lys
```